(12) United States Patent
Lee et al.

(10) Patent No.: US 11,441,142 B2
(45) Date of Patent: Sep. 13, 2022

(54) FLS VARIANT HAVING INCREASED ACTIVITY

(71) Applicant: KONKUK UNIVERSITY INDUSTRIAL COOPERATION CORPORATION, Seoul (KR)

(72) Inventors: Jung-Kul Lee, Seoul (KR); Liaoyuan Zhang, Seoul (KR); Jing-Lin Li, Seoul (KR)

(73) Assignee: KONKUK UNIVERSITY INDUSTRIAL COOPERATION CORPORATION, Seoul (KR)

(*) Notice: Subject to any disclaimer, the term of this patent is extended or adjusted under 35 U.S.C. 154(b) by 0 days.

(21) Appl. No.: 16/956,064

(22) PCT Filed: Nov. 23, 2018

(86) PCT No.: PCT/KR2018/014538
§ 371 (c)(1),
(2) Date: Jun. 19, 2020

(87) PCT Pub. No.: WO2019/124782
PCT Pub. Date: Jun. 27, 2019

(65) Prior Publication Data
US 2021/0207117 A1    Jul. 8, 2021

(30) Foreign Application Priority Data

Dec. 20, 2017 (KR) .......... 10-2017-0176269
Jan. 19, 2018 (KR) .......... 10-2018-0006982
Jan. 19, 2018 (KR) .......... 10-2018-0007006
Feb. 21, 2018 (KR) .......... 10-2018-0020623

(51) Int. Cl.
| | |
|---|---|
| *C12N 9/88* | (2006.01) |
| *C12N 9/00* | (2006.01) |
| *C12N 9/02* | (2006.01) |
| *C12P 7/18* | (2006.01) |
| *C12P 7/26* | (2006.01) |
| *C12P 7/16* | (2006.01) |
| *C12N 9/04* | (2006.01) |

(52) U.S. Cl.
CPC ............ *C12N 9/88* (2013.01); *C12N 9/0004* (2013.01); *C12N 9/0006* (2013.01); *C12N 9/93* (2013.01); *C12P 7/16* (2013.01); *C12P 7/18* (2013.01); *C12P 7/26* (2013.01); *C12Y 101/01001* (2013.01); *C12Y 101/01004* (2013.01); *C12Y 106/03001* (2013.01); *C12Y 402/01028* (2013.01)

(58) Field of Classification Search
None
See application file for complete search history.

(56) References Cited

U.S. PATENT DOCUMENTS

2013/0196359 A1* 8/2013 Siegel .................. C12N 9/88
435/26
2017/0159081 A1  6/2017 Bremond et al.

FOREIGN PATENT DOCUMENTS

| CN | 104017758 A | 9/2014 |
|---|---|---|
| CN | 107129959 A | 9/2017 |
| CN | 107475281 A | 12/2017 |
| KR | 10-2017-0041768 A | 4/2017 |
| KR | 10-2017-0065242 A | 6/2017 |

OTHER PUBLICATIONS

Alignment of SEQ ID No. 9 of US20130196359 to SEQ ID No. 8 of the instant application (Year: 2013).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Mitsuru Matsubara et al., "Fermentative production of 1-propanol from D-glucose, L-rhamnose and glycerol using recombinant *Escherichia coli*", Journal of Bioscience and Bioengineering, 2016, pp. 421-426, vol. 122, No. 4.
Liaoyuan Zhang et al., "Artificial synthetic pathway for acetoin, 2,3-butanediol, and 2-butanol production from ethanol using cell free multi-enzyme catalysis", Green Chemistry, Nov. 23, 2017, pp. 1-43.
International Search Report for PCT/KR2018/014538 dated May 29, 2019 (PCT/ISA/210).

* cited by examiner

*Primary Examiner* — Christian L Fronda
(74) *Attorney, Agent, or Firm* — Sughrue Mion, PLLC

(57) ABSTRACT

In a method for producing acetoin, butanediol, or butanol from ethanol according to the present invention, a cell-free catalysis method was used by designing an artificial synthetic pathway so that proteins of NOX, EtDH, FLS, BDH, and DDH and variant proteins thereof exhibit cascade catalytic activity as enzymes. Compared to existing fermentation methods using microorganisms, the production method according to the present invention does not require cell growth and has a short synthetic pathway, a fast reaction rate, high yield and productivity, adjustment of targeted reaction conditions is convenient, and butanol may be effectively produced. Moreover, same may be reused numerous times by fixing the proteins to nano-particles, and are also effective for producing acetoin, butanediol, or butanol, thus being economical. Therefore, the production method may be usefully adopted in the relevant industries requiring acetoin, butanediol, or butanol.

2 Claims, 2 Drawing Sheets

Specification includes a Sequence Listing.

FLS VARIANT HAVING INCREASED ACTIVITY

CROSS REFERENCE TO RELATED APPLICATIONS

This application is a National Stage of International Application No. PCT/KR2018/014538 filed Nov. 23, 2018, claiming priority based on Korean Patent Application No. 10-2017-0176269 filed Dec. 20, 2017, Korean Patent Application No. 10-2018-0006982 filed Jan. 19, 2018, Korean Patent Application No. 10-2018-0007006 filed Jan. 19, 2018 and Korean Patent Application No. 10-2018-0020623 filed Feb. 21, 2018, the entire contents of which are incorporated herein by reference.

TECHNICAL FIELD

The present disclosure relates to a production method of acetoin, butanediol or butanol from ethanol and various applications thereof.

BACKGROUND ART

Interest in bioethanol, biodiesel, biogas and butanol, which are representative of bioenergy is increasing. All of the bioenergy of types as mentioned above may be used as fuel for electricity generation or transportation. However, due to some shortcomings thereof in terms of performance and a production method, interest in hydrocarbon-type compounds as a new renewable energy resource is increasing. Acetoin, butanediol or butanol is an intermediate compound with a wide range of applications, such as cosmetics, perfumes, hormones, hygiene, industrial coatings, paint additives, textiles, plastic monomers, medical supplies, vitamins, antibiotics, and pesticides, and its utility is very high. In order to produce butanol at an industrially useful level using microorganisms, a fermentation process must be performed. Selectivity, yield and productivity (i.e. a production amount per unit time) of acetoin, butanediol or butanol should all be excellent. Excessive repeated experiments have been required to discover microorganisms satisfying these conditions.

DISCLOSURE

Technical Problem

A purpose of the present disclosure is to provide a method of producing acetoin, butanediol or butanol from ethanol.

Technical Solution

The present disclosure provides a production method of acetoin, butanediol or butanol from ethanol.

Advantageous Effects

In a method for producing acetoin, butanediol, or butanol from ethanol according to the present disclosure, a cell-free catalysis method was used by designing an artificial synthetic pathway so that proteins of NOX, EtDH, FLS, BDH, and DDH and variant proteins thereof exhibit cascade catalytic activity as enzymes. Compared to existing fermentation methods using microorganisms, the production method according to the present disclosure does not require cell growth and has a short synthetic pathway, a fast reaction rate, high yield and productivity, adjustment of targeted reaction conditions is convenient, and butanol may be effectively produced. Moreover, same may be reused numerous times by fixing the proteins to nano-particles, and are also effective for producing acetoin, butanediol, or butanol, thus being economical.

MODES OF THE INVENTION

Figure 1A:
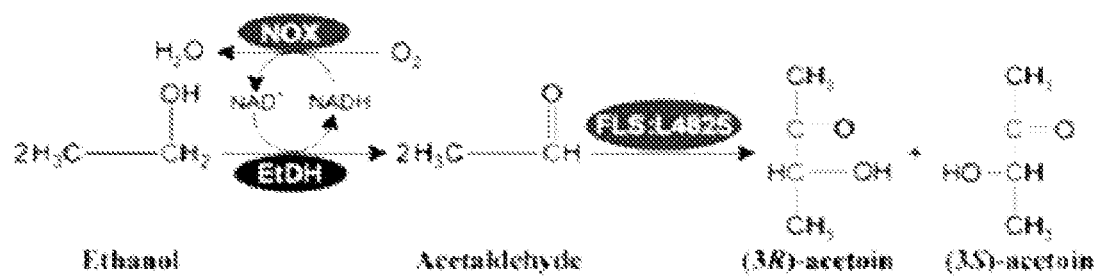
FIG. 1A schematically shows a method of producing acetoin from ethanol using a cell-free multi-catalyst system containing an optimal enzyme in accordance with the present disclosure.

The present disclosure provides a FLS amino acid variant including at least one variant selected from a group consisting of variants in which 482-th leucine is substituted with serine, arginine and glutamic acid in FLS (formolase) amino acid represented by SEQ ID NO: 8.

As used herein, the term "FLS (formolase)" catalyzes carboligation of three 1-carbon formaldehyde molecules into one 3-carbon dihydroxyacetone molecule. For a purpose in accordance with the present disclosure, FLS and variants thereof produce acetoin using acetaldehyde produced during alcohol metabolism as a substrate, and produce 2,3-butanediol using acetoin as a substrate and produce butanol using the 2,3-butanediol as a substrate, but is not limited thereto.

As used herein, the term "FLS amino acid variant" means a variant in which at least one amino acid among wild-type FLS amino acids is replaced, inserted, removed or modified. The FLS may be encoded into a nucleic acid sequence represented by SEQ ID NO: 7. The variant (FLS:L482S) in which the 482-th leucine is substituted with serine in the FLS is represented by the amino acid of SEQ ID NO: 10. The variant (FLS:L482R) in which 482-th leucine is substituted with arginine is represented by the amino acid of SEQ ID NO: 11. The variant (FLS:L482E) in which 482-th leucine is substituted with glutamic acid is represented by the amino acid of SEQ ID NO: 12. The FLS amino acid variant may further include one or more selected from a group consisting of a variant in which 396-th threonine in the FLS amino acid is substituted; a variant in which 446-th threonine in the FLS amino acid is substituted; a variant in which 473-th methionine in the FLS amino acid is substituted; a variant in which 477-th serine in the FLS amino acid is substituted; and a variant in which 499-th leucine in the FLS amino acid is substituted. As long as the purpose of converting acetaldehyde produced in the metabolism process of ethanol to acetoin is achieved, the present disclosure is not limited thereto. The FLS is derived from *Pseudomonas fluorescens*. The present disclosure is not limited thereto.

In one embodiment of the present disclosure, based on analyzing of the structure of FLS in FLS variants in accordance with the present disclosure, six residual hot spots (T396, T446, M473, 5477, L482 and L499) were discovered. Among them, in molecular interaction with acetaldehyde as a substrate, the active site residue was identified as W480. It was identified that the variant FLS:L482S bound more strongly to a substrate than FLS, and the binding was hydrogen binding.

Further, the present disclosure provides a gene encoding the FLS amino acid variant. Further, the present disclosure provides a recombinant vector containing at least one gene selected from a group consisting of NOX (NADH oxidase) gene, EtDH (ethanol dehydrogenase) gene, EtDH variant gene, FLS (formolase) gene, gene encoding the FLS amino acid variant, BDH (2,3-butanediol dehydrogenase) gene, BDH variant gene, DDH (diol dehydratase) gene and DDH variant gene.

As used herein, the term "NOX (NADH oxidase)" uses oxygen as the substrate for the purpose in accordance with the present disclosure, and induces oxidation of NADH to reproduce $NAD^+$. The reproduced $NAD^+$ may be used by EtDH as a coenzyme.

As used herein, the term "EtDH (ethanol dehydrogenase)" uses ethanol as a substrate for the purpose in accordance with the present disclosure, and may dehydrogenate ethanol using $NAD^+$ and/or $NADP^+$ as a coenzyme. Then, the EtDH may induce acetaldehyde production so that FLS may produce acetoin using the acetaldehyde as a substrate.

As used herein, the term "BDH (2,3-butanediol dehydrogenase)" catalyzes the production of 2,3-butanediol using NADPH as a coenzyme and using acetoin as a substrate for the purpose in accordance with the present disclosure. Further, butanone is catalyzed by DDH using the produced 2,3-butanediol as a substrate. When BDH is catalytic-reacted using butanone as a substrate, butanol may be finally produced.

As used herein, the term "DDH (diol dehydratase)" may catalyze the production of butanone using vitamin B12 as a coenzyme and using 2,3-butanediol as the substrate for the purpose in accordance with the present disclosure.

The NOX gene is derived from *Lactobacillus rhamnosus*, and the EtDH gene or EtDH variant gene may be derived from *Cupriavidus necator*. Further, the BDH gene or BDH variant gene may be derived from *Clostridium autoethanogenum*, and the DDH (diol dehydratase) gene and DDH variant gene may be derived from *Lactobacillus brevis*. However, as long as enzyme for butanol production in accordance with the present disclosure is realized, the present disclosure is not limited thereto.

The NOX gene has a nucleic acid sequence represented by SEQ ID NO: 1. EtDH gene has a nucleic acid sequence represented by SEQ ID NO: 3. In the variant of the EtDH, a 46-th aspartic acid of EtDH represented by the amino acid sequence of SEQ ID NO: 4 is substituted with glycine (EtDH:D46G). The variant of the EtDH may be expressed by the nucleic acid sequence of SEQ ID NO: 5 and the amino acid of SEQ ID NO: 6.

In the variant of the BDH, a 199-th serine of BDH represented by the amino acid sequence of SEQ ID NO: 14 is substituted with alanine (BDH:S199A). The variant of the BDH may be expressed by the nucleic acid sequence of SEQ ID NO: 15 and an amino acid sequence of SEQ ID NO: 16.

The DDH gene has a nucleic acid sequence represented by SEQ ID NO: 17. The variant of the DDH may include one or more single or multiple variants selected from a group consisting of a variant (DDH:S302A) in which 302-th serine of DDH amino acid of SEQ ID NO: 18 is substituted with alanine; a variant (DDH:Q337A) in which 337-th glutamine is substituted with alanine; and a variant (DDH:F375I) in which 375-th phenylalanine is substituted with isoleucine. However, the present disclosure is not limited thereto.

The multiple variant may include at least one selected from a group consisting of a variant (DDH:Q337A/F375I) in which 337-th glutamine of DDH amino acid of SEQ ID NO: 18 is substituted with alanine, and 375-th phenylalanine is substituted with isoleucine; a variant (S302A/F375I) in which 302-th serine is substituted with alanine and 37-th glutamine is substituted with alanine; and a variant (S302A/Q337A/F375I) in which 302-th serine is substituted with alanine, 337-th glutamine is substituted with alanine, and 375-th phenylalanine is substituted with isoleucine. However, the present disclosure is not limited thereto.

The variant of the DDH may express dhaR as a reactivating factor of DDH.

In one embodiment of the present disclosure, a plasmid was prepared to express each protein and variants thereof. Further, EtDH or EtDH:D46G variant expressing plasmids and vector maps were prepared. Further, FLS:L482S, BDH:S199A, DDH:Q337A/F375I variant expressing plasmids and vector maps were prepared (Tables 1 and 2).

In one embodiment of the present disclosure, based on a result of analyzing the structure of DDH and its variant in accordance with the present disclosure, it was identified that in the molecular interaction with 2,3-butanediol as a substrate, the active site residue was E171. The variant DDH:Q337A/F375I was more strongly bound to the substrate than DDH was. The finding was hydrogen binding and water bridges. Further, it was identified that DDH and its variant in accordance with the present disclosure exhibit stereoselectivity, and do not produce butanone using (2R,3R)-2,3-butanediol and (2S,3S)-2,3-butanediol as a substrate, but produce butanone using only meso-2,3-butanediol as a substrate.

In one embodiment of the present disclosure, it was identified based on a result of the thermal stability that when the protein in accordance with the present disclosure is used as an enzyme, EtDH, EtDH:D46G, EtDH:D46G, EtDH:D46G, FLS, FLS:L482S, BDH:S199A, BDH:S199A, DDH:Q337A/F375 containing dhaR, and NOX protein exhibit thermal stability even at high 30 to 45 degrees C. In particular, it was identified that the reaction activity thereof was excellent at 30 degrees C.

Further, the present disclosure provides transformed microorganisms into which the recombinant vector has been introduced.

The transformant in accordance with the present disclosure may be constructed by introducing a vector into a host cell such that the vector acts as a promoter.

Further, the present disclosure provides a butanol production method including purifying and reacting a protein produced in the transformed microorganism.

The butanol may be at least one selected from a group consisting of 2-butanol, n-butanol, isobutanol and tert-butanol, and may be preferably 2-butanol, but is not limited thereto. In the production method, butanol is produced by performing cascade catalysis on a protein produced from the transformed microorganism in a cell-free state. In the method, ethanol is used as a substrate, but is not limited thereto.

The production method further includes using at least one coenzyme selected from a group consisting of $NAD^+$, $NADP^+$, vitamin B12 and thiamine pyrophosphate (TPP) as coenzyme, but a treatment concentration or amount thereof is not limited. The production method further includes using at least one metal ion selected from a group consisting of metal ions $Mg^{2+}$, $Mn^{2+}$, $Ca^{2+}$, $Fe^{2+}$, $Ni^{2+}$, and $Zn^{2+}$. Preferably, $Mg^{2+}$, $Mn^{2+}$, $Ca^{2+}$, $Fe^{2+}$ and $Ni^{2+}$ may induce a catalytic reaction more efficiently, but are not limited thereto as long as butanol production is realized.

The production method produces butanol under the condition of pH 5.0 to 9.0, preferably, the conditions of 6.5 to 8.5. However, as long as the purpose of the butanol production is realized, the present disclosure is not limited thereto. The production method produces butanol at 16 to 45 degrees C., preferably 25 to 42 degrees C., but is not limited thereto.

According to the present disclosure, an artificial synthetic pathway using cascade enzymes to produce butanol as a $C_4$ compound from ethanol is designed. As the cascade enzymes, NOX, EtDH, FLS, BDH and DDH and variants thereof are selected. Specifically, NOX uses oxygen as the substrate to induce oxidation of NADH to reproduce $NAD^+$. The reproduced $NAD^+$ is used as a coenzyme by EtDH. EtDH and its variant use ethanol as a substrate and use $NAD^+$ and/or $NADP^+$ as coenzyme to induce dehydrogenation of ethanol to produce acetaldehyde. Then, FLS and its variant induce acetoin production using acetaldehyde as a substrate. BDH catalyzes production of 2,3-butanediol using acetoin as a substrate and using NADPH as a coenzyme. DDH catalyzes production of butanone using vitamin $B_{12}$ as a coenzyme and using 2,3-butanediol as the substrate for the purposes in accordance with the present disclosure. Thereafter, the BDH is catalytic-reacted using catalyzed butanone as a substrate, to finally produce butanol.

The present disclosure achieved the purpose of artificial synthetic of butanol from ethanol using a simplified pathway in vitro using the cell-free multi-enzyme catalysis (CFME) method. When using the cell-free multi-enzyme catalysis method, problems such as low target product yield, unwanted by-product production, and intracellular transport restrictions in the conventional metabolic engineering using cells, such as fermentation methods in which bacteria and recombinant microorganisms are cultured may be solved, such that cell growth is not required, and advantages such as short synthetic pathway, fast reaction rate, high yield and productivity, and control of desired reaction conditions are achieved.

In one embodiment of the present disclosure, according to a method of Example 7-6, an optimal butanol production method uses cell-free multi-enzyme catalysis according to the artificial synthetic pathway designed in the present disclosure, and uses ethanol as the substrate. A reaction mixture to which NOX, EtDH:D46G, FLS:L482S, BDH:S199A, DDH:Q337A/F375I as enzymes, and $NAD^+$, $NADP^+$, TPP, vitamin $B_{12}$, and $Mg^{2+}$ as coenzymes are added is used to effectively induce 2-butanol production.

Further, the present disclosure provides a butanol production method including immobilizing and reacting a protein produced from the transformed microorganism to nano-particles.

The nano-particle has silicon oxide attached thereto and reacts with glutaraldehyde. However, the present disclosure is not limited thereto, as long as the purpose of producing butanol by attaching the protein in accordance with the present disclosure to the nano-particle is achieved. The immobilized protein nano-particles may be reused, and may be preferably reused 1 to 30 times, more preferably, 1 to 20 times, but is not limited thereto.

In one embodiment of the present disclosure, according to a method of Example 7-6, an optimal butanol production method uses cell-free multi-enzyme catalysis according to the artificial synthetic pathway designed in the present disclosure, and uses ethanol as the substrate. A reaction mixture to which NOX, EtDH:D46G, FLS:L482S, BDH:S199A, DDH:Q337A/F375I as enzymes, and $NAD^+$, $NADP^+$, TPP, vitamin $B_{12}$, and $Mg^{2+}$ as coenzymes are added is used to effectively induce 2-butanol production. The enzyme is attached and immobilized to the nano-particles to induce butanol production. In this connection, butanol is effectively produced even after reuse of the enzyme-immobilized nano-particles.

The present disclosure will be described in more detail based on the following examples. However, the following examples are only intended to specify the contents in accordance with the present disclosure, and the present disclosure is not limited thereto.

<Example 1> Experiment Preparation and Experiment Method

<1-1> Enzyme and Reagent Purchase

DNA Polymerase High Fidelity and T4 DNA ligase as restriction enzymes were purchased from TaKaRa Biotech (Shiga, Japan) and New England Biolabs (Ipswich, Mass., USA), respectively. DNA and protein markers were purchased from Tiangen Biotech (Shanghai, China). Isopropyl-beta-D-thiogalactopyranoside (IPTG), dithiothreitol (DTT) and dimethyl sulfoxide (DMSO) were purchased from Sigma-Aldrich (St. Louis, Mo., USA) and Sinopharm (Shanghai, China), respectively. As a control, (3S/3R)-acetoin (acetoin), (2S,3S)-2,3-butanediol, (2R,3R)-2,3-butanediol, meso-2,3-butanediol, butanone and 2-butanol were purchased from Sigma-Aldrich. All other reagents had an analytical grade and were commercially available, unless otherwise specified.

<1-2> Bacterial Strain, Plasmid and Bacterial Growth Conditions

Strains and plasmids used in the present disclosure are shown in Table 1 below. *Escherichia coli* DH5α and BL21 (DE3) were used as a cloning and expressing host. Culturing thereof was performed at 37 degrees C. An expression vector was prepared using plasmid pET28a. Luria-Bertani (LB) medium was used for strain culture and recombinant protein expression. Kanamycin was added to the medium to incubate the recombinant strain with a final concentration of 50 µg $mL^{-1}$.

TABLE 1

| | Relevant genotype and description |
|---|---|
| Strains | |
| *E. coli* DH5α | Host of plasmid for cloning |
| *E. coli* BL21(DE3) | Host of plasmid for expression, F−, ompT, hsdSB(rB−mB−), gal(λ c 1 857, ind1, Sam7, nin5, lacUV-T7 gene1), dcm(DE3) |
| Plasmids | |
| pET28a | Expression vector, $Km^R$ |
| pET-EtDH | pET28a carries EtDH gene |
| pET-EtDH:D46G | pET28a carries EtDH mutant gene |
| pET-FLS | pET28a carries FLS gene |
| pET-FLS:L482S | pET28a carries FLS mutant gene |
| pET-FLS:L482R | pET28a carries FLS mutant gene |
| pET-FLS:L482E | pET28a carries FLS mutant gene |
| pET-BDH | pET28a carries BDH gene |
| pET-BDH:S199A | pET28a carries BDH mutant gene |

TABLE 2

| Strains | Relevant genotype and description |
|---|---|
| pET-DDH | pET28a carries DDH gene |
| pET-DDH:S302A | pET28a carries DDH mutant gene |
| pET-DDH:Q337A | pET28a carries DDH mutant gene |
| pET-DDH:F375I | pET28a carries DDH mutant gene |
| pET-DDH:S302A/Q337A | pET28a carries DDH mutant gene |
| pET-DDH:S302A/F375I | pET28a carries DDH mutant gene |
| pET-DDH:Q337A/F375I | pET28a carries DDH mutant gene |
| pET-DDH:S302A/Q337A/F375I | pET28a carries DDH mutant gene |
| pET-dhaR | pET28a carries dhaR gene |
| pET-DDH:dhaR | pET28a carries DDH and dhaR genes |
| pET-NOX | pET28a carries NOX gene |

<1-3> Recombinant Protein Expressing and Purification of Cascade Enzymes

In order to produce acetoin and 2,3-butanediol as $C_4$ compounds from ethanol, and finally to produce 2-butanol, cascade enzymes were used. Genes of EtDH (ethanol dehydrogenase), FLS (formolase), BDH (2,3-butanediol dehydrogenase), DDH (diol dehydratase), and NOX (NADH oxidase) were respectively derived from *Cupriavidus necator* [T. Y. Wu, et al., Appl. Microbiol. Biotechnol. 2016, 100, 1], *Pseudomonas fluorescens* [J. Siegel, et al., Proc. Natl. Acad. Sci. U.S.A, 2015, 112, 3704], *Clostridium autoethanogenum* [M. Kopke, et al., Appl. Environ. Microbiol., 2014, 80, 3394], *Lactobacillus brevis* [(Z. Chen, et al., Bioresource Technol., 2015, 197, 260), (M. Yamanishi, et al., FEBS. J., 2012, 279, 793)], and *Lactobacillus rhamnosus* [Y. W. Zhang, et al., Enzyme Microb. Tech., 2012, 50, 255]. They were synthesized in General Biosystems, Inc. (Anhui, China). Further, each of the genes was cloned into the expressing plasmid pET28a. A protein expressing plasmid was introduced into *E. coli* BL21 (DE3). Each recombinant *E. coli* BL21 (DE3) containing each of pET-EtDH, pET-FLS, pET-BDH, pET-DDH, pET-dhaR, pET-DDH-dhaR, and pET-NOX was incubated at 37 degrees C. in LB medium containing 0.5 mM IPTG when an optical density at 600 nm was 0.6. After induction at 18 degrees C. for 24 hours, cells were obtained by centrifugation and crushed by sonication in an ice bath. The cell lysate was centrifuged at 8000×g for 10 minutes to remove cell debris. To obtain EtDH, FLS, BDH, dhaR and NOX enzymes, soluble fractions were purified using HisTrap HP column according to purification protocol (GE Healthcare, Little Chalfont, UK). DDH purification was carried out by a conventional method [M. Seyfried, et al., J. Bacteriol., 1996, 178, 5793]. Each of the purified enzymes was subjected to ultrafiltration and concentrated and desalted, and then detected using SDS-PAGE.

<1-4> Preparation of Enzyme Variants

The variants of the respective EtDH, FLS, BDH and DDH enzymes were prepared and expressed and purified. Further, in order to prepare EtDH or BDH variant, EtDH:D46G and BDH:S199A variants were subjected to site-directed mutagenesis using EtDH1/EtDH2 and BDH1/BDH2 primers shown in Table 3 below. Recombinant plasmids pET-EtDH and pET-BDH containing wild-type EtDH and BDH genes were used as DNA templates for PCR amplification, respectively. After transforming the recombinant plasmid containing the corrected variant gene into *E. coli* BL21 (DE3), colonies were selected to have kanamycin resistance and used for protein expression. After purification of each protein, activities and kinetic parameters of EtDH and BDH variants were measured. Further, in order to increase the catalyst efficiency of the FLS enzyme, the FLS structure (PDB No.: 4QPZ) was input to the HotSpot Wizard 2.0 server to find a new mutation region. Thus, a hot spot was analyzed [(J. Siegel, et al., Proc. Natl. Acad. Sci. U.S.A, 2015, 112, 3704), (J. Bendl, et al., Acids Res., 2016, 44, 479)]. For six residual hot spots (T396, T446, M473, S477, L482 and L499), site-directed mutations were induced using the FLS1-FLS12 primers in Table 2 below. Recombinant plasmid pET-FLS containing wild-type FLS was used as a DNA template. The recombinant plasmid containing the mutant gene was transformed into *E. coli* BL21 (DE3). The FLS variant was screened using a whole-cell biocatalytic method using acetaldehyde as a substrate. Specifically, when the colony was inoculated in LB medium and then the optical density reached 0.6 at 600 nm, 0.5 mM IPTG was added thereto and the culture was carried out at 18 degrees C. for 24 hours. Thus, protein expression was induced. The cells were obtained by centrifugation. The cells were subjected to the whole-cell biocatalytic method using a reaction mixture containing 50 mM phosphate buffer solution (pH 8.0), 100 mM acetaldehyde and 40 $gL^{-1}$ wet cell weight (WCW) under conditions of 30 degrees C. for 6 hours. Further, the DDH variant was prepared. For the expression of dhaR as the reactivating factor of the DDH, DDH variants including S302A, Q337A, F375I, S302A/Q337A, S302A/F375I, Q337A/F375I and S302A/Q337A/F375I were prepared, and were compared with wild-type DDH enzymes to identify catalyst efficiency thereof. The site-directed mutation was induced and prepared using the DDH1-DDH6 primer of Table 2 below. The pET-DDH-dhaR recombinant plasmid containing the wild-type DDH and the dhaR gene as an activating factor thereof were used as a DNA template for PCR amplification. To induce expression of each protein, the PCR product was transformed into *E. coli* BL21 (DE3) which in turn was cultured in the LB medium containing 0.5 mM IPTG for 18 degrees C. and 24 hours. The variant was used to evaluate the catalytic activity using the whole-cell biocatalytic analysis using meso-2,3-butanediol as a substrate. The reaction mixture contained 50 mM HEPES buffer solution (pH 7.0), 50 mM meso-2,3-b butanediol, 20 μM coenzyme $B_{12}$ and 40 $gL^{-1}$ wet cell weight. The whole-cell biocatalytic method was performed at 30 degrees C. for 6 hours in the dark condition. The butanone product was quantified using gas chromatography. Table 4 shows nucleic acid sequences for the enzymes and some variants thereof and strains from which they are derived.

TABLE 3

| Primers | Sequence (5'-3') | Mutation site | seq No. |
|---|---|---|---|
| EtDH1 | GATTGTTACCGGTGCTGGCC TGCATAAATG | D46G | 25 |
| EtDH2 | CATTTTATGCAGGCCAGCACC GGTAACAATC | D46G | 26 |
| FLS1 | GGTAGCGGATGGTGGCCTGN NNTATCTCTGGCTGTCC | T396 | 27 |
| FLS2 | GGACAGCCAGAGATANNNCA GGCCACCATCCGCTACC | T396 | 28 |
| FLS3 | CCGCCGCACGATCCTTGTGN NNGGCGATGGCTCGGTG | T446 | 29 |
| FLS4 | CACCGAGCCATCGCCNNNCA CAAGGATCGTGCGGCGG | T446 | 30 |
| FLS5 | GCCGCTGATCGTCATCATCN NNAACAACCAAAGCTGG | M473 | 31 |

TABLE 3-continued

| Primers | Sequence (5'-3') | Mutation site | seq No. |
|---|---|---|---|
| FLS6 | CCAGCTTTGGTTGTTNNNGATGATGACGATCAGCGGC | M473 | 32 |
| FLS7 | CATCATCATGAACAACCAANNNTGGGGGTGGACATTG | S477 | 33 |
| FLS8 | CAATGTCCACCCCANNNTTGGTTGTTCATGATGATG | S477 | 34 |
| FLS9 | CCAAAGCTGGGGGTGGACANNNCATTTCCAGCAATTG | L482 | 35 |
| FLS10 | CAATTGCTGGAAATGNNNTGTCCACCCCCAGCTTTGG | L482 | 36 |
| FLS11 | TCGCGTGACGGGCACCCGTNNNGAAAATGGCTCCTAT | L499 | 37 |
| FLS12 | ATAGGAGCCATTTTCNNNACGGGTGCCCGTCACGCGA | L499 | 38 |
| BDH1 | GAATTATCGGTGTTGGAGCCAGACCTGTTTGTGTTG | S199A | 39 |
| BDH2 | CAACACAAACAGGTCTGGCTCCAACACCGATAATTC | S199A | 40 |
| DDH1 | CTCGAAAACGGTGGGGTTGCTTGTATTGGGATTCCAG | S302A | 41 |
| DDH2 | CTGGAATCCCAATACAAGCAACCCCACCGTTTTGGAG | S302A | 42 |
| DDH3 | ATGTGCGTCTGCTAATGACGCAGCGTTCTCCCATTCTG | Q337A | 43 |
| DDH4 | CAGAATGGGAGAACGCTGCGTCATTAGCAGACGCACAT | Q337A | 44 |
| DDH5 | CACCTAACTATGACAACACGATTGCGGGTCAAACACCG | F375I | 45 |
| DDH6 | CGGTGTTTGACCCCGCAATCGTGTTGTCATAGTTAGGT | F375I | 46 |

TABLE 4

| Nucleic acid sequence of gene or variant thereof | Strain from which gene is derived | Nucleic acid sequence NO | Amino acid sequence NO |
|---|---|---|---|
| NOX(NADH oxidases) | Lactobacillus rhamnosus | 1 | 2 |
| EtDH(ethanol dehydrogenase) | Cupriavidus necator | 3 | 4 |
| EtDH D46G | | 5 | 6 |
| FLS(formolase) | Pseudomonas fluorescens | 7 | 8 |
| FLS:L482S | | 9 | 10 |
| FLS:L482R | | | 11 |
| FLS:L482E | | | 12 |
| BDH(2,3-butanediol dehydrogenase) | Clostridium autoethanogenum | 13 | 14 |
| BDH: S199A | | 15 | 16 |
| DDH(diol dehydratase) | Lactobacillus brevis | 17 | 18 |
| DDH:S302A | | | 19 |
| DDH:Q337A | | | 20 |
| DDH:F375I | | | 21 |
| DDH:Q337A/F375I | | 22 | 23 |
| dhaR | | 24 | |

<1-5> Enzyme Activity Analysis

For the analysis of EtDH enzyme activity, EtDH enzyme and variant thereof reacted with a reaction mixture containing 100 mM glycine-NaOH buffer solution (pH 9.5), 5 mM $Mg^{2+}$, 3 mM $NAD^+/NADP^+$ and 10 mM ethanol at 25 degrees C. Activity thereof was identified based on a $NAD^+/NADP^+$ reduction at 340 nm using a spectrophotometer (UV-1800, MAPADA, Shanghai, China). One unit of EtDH activity was defined as an amount of enzyme required to reduce 1 μmol of $NAD^+/NADP^+$ per minute. For FLS enzyme activity analysis, FLS enzyme and its variant reacted with a reaction mixture containing 100 mM phosphate buffer solution (pH 8.0), 1 mM $Mg^+$, 0.1 mM TPP and 20 mM acetaldehyde. After the reaction, the reaction product was left at room temperature for 1 hour. The concentration of acetoin in acetaldehyde was measured using VP reaction, and was calculated using a standard acetoin calibration curve. For analysis of BDH enzyme activity, BDH enzyme and its variant reacted with a reaction mixture containing 50 mM tris-HCl buffer solution (pH 7.5), 0.2 mM NADPH, 1 mM DTT, and 20 mM acetoin or 5 mM butanone at room temperature. Activity thereof was identified based on the oxidation rate of NADPH at 340 nm using a spectrophotometer (UV-1800, MAPADA). One unit of BDH activity was defined as the amount of enzyme required to oxidize 1 μmol NADPH per minute. For analysis of DDH enzyme activity, DDH enzyme and a variant thereof including the activating factor dhaR reacted with a reaction mixture containing 50 mM phosphate buffer solution (pH 7.0), 1 mM coenzyme $B_{12}$, 100 mM ATP, 1 mM $Mg^{2+}$ and 50 mM meso-2,3-butanediol. The reaction occurred at room temperature for 1 hour in the dark condition. Then, the reaction was stopped by adding citrate buffer (100 mM, pH 3.6) thereto at the same volume. Butanone product was measured by gas chromatography. One unit of DDH activity was defined as the amount of the enzyme for producing 1 μmol butanone from meso-2,3-butanediol per minute. For analysis of NOX enzyme activity, NOX enzyme reacted with a reaction mixture containing 50 mM HEPES-NaOH buffer (pH 8.0) and 0.2 mM NADH at room temperature. Activity thereof was identified based on the oxidation rate of NADH at 340 nm using a spectrophotometer (UV-1800, MAPADA). One unit of NOX activity was defined as the amount of the enzyme required to oxidize 1 μmol NADH per minute.

<1-6> VP (Voges-Proskauer) Reaction

Each group treated under each condition was centrifuged at 4° C. for 5 minutes at 10,000×g. To analyze the acetoin concentration of each treated group and quantify the same in the VP reaction, 0.3 mL of a diluted sample, 0.3 mL of 0.5% creatine, 0.3 mL of 5% alpha naphthol and 0.3 mL of 5% NaOH were added to a 10 mL tube which in turn was shaken gently at 30 degrees C. for 30 minutes. The optical density of the reaction solution was measured at 520 nm using a spectrophotometer (UV-1800, MAPADA) and acetoin concentration was calculated using a calibration curve. A calibration graph was measured in a range of a corresponding optical density at 520 nm after the VP reaction at the standard acetoin concentration and the 0.04 to 0.4 mM range of the acetoin concentration.

<1-7> Measurement of Kinetic Parameters

The kinetic parameters of EtDH and EtDH:D46G were identified by reacting the EtDH and EtDH:D46G with a reaction mixture containing 100 mM glycine-NaOH buffer solution (pH 9.5), 5 mM $Mg^{2+}$, 3 mM $NAD^+$/$NADP^+$ and 0.5 to 100 mM ethanol at room temperature. The kinetic parameters of FLS and variants thereof were identified by reacting FLS and variants thereof with a reaction mixture containing 100 mM phosphate buffer solution (pH 8.0), 1 mM $Mg^+$, 0.1 mM TPP and 0.5 to 20 mM acetaldehyde at room temperature. The kinetic parameters of BDH and BDH:S199A were identified by reacting BDH and BDH:S199A with a reaction mixture containing 50 mM Tris-HCl buffer solution (pH 7.5), 0.2 mM NADPH, 1 mM DTT; 0.5 to 100 mM acetoin or 0.5 to 10 mM butanone at room temperature. The Km and kcat values were identified using nonlinear regression fitting of the Michaelis-Menten equation and the fitting were repeated three times.

<1-8> Cell-Free Multi-Enzyme Catalysis System

Figure 1B:
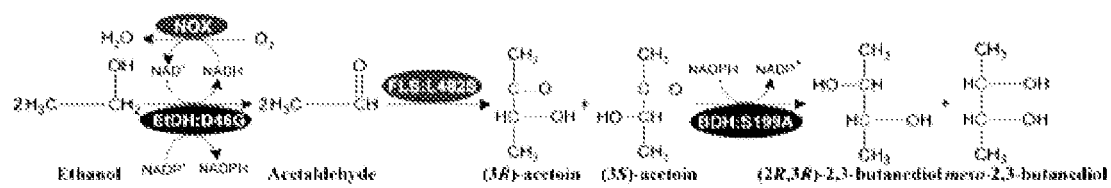
FIG. 1B schematically shows a method of producing 2,3-butanediol from ethanol using a cell-free multi-catalyst system containing an optimal enzyme in accordance with the present disclosure.
Figure 1C:
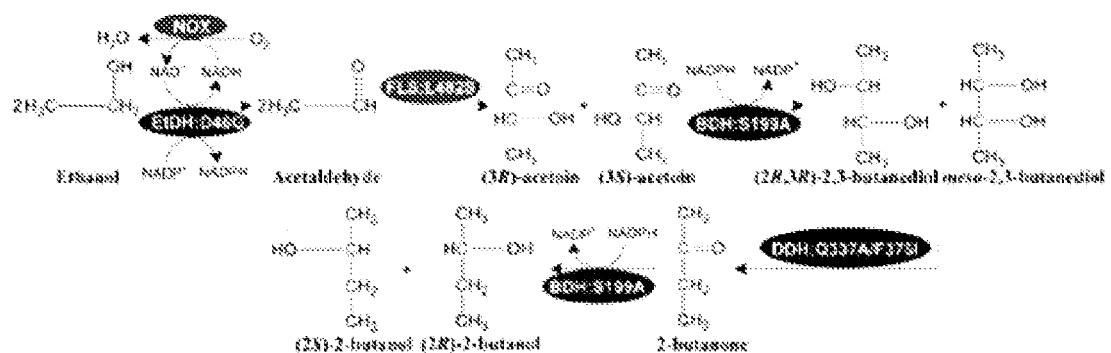
FIG. 1C schematically shows a method of producing 2-butanol from ethanol using a cell-free multi-catalyst system containing an optimal enzyme in accordance with the present disclosure.

As shown in FIG. 1A to FIG. 1C, synthesis of acetoin, 2,3-butanediol or 2-butanol from ethanol using cell-free multi-enzyme catalysis was conducted using a 0.5-mL reaction mixture containing substrate, coenzyme, metal ions and corresponding enzyme. Reaction conditions including temperature, pH, coenzyme and metal ions were controlled to optimal conditions to increase the flux of an artificial reaction path. The optimal reaction conditions for production of acetoin, 2,3-butanediol or 2-butanol are as follows. The acetoin production was conducted by reacting 0.5-mL reaction mixture containing 50 mM HEPES buffer (pH 8.0), 1 mM $NAD^+$, 0.1 mg $mL^{-1}$ EtDH, 0.2 mg $mL^{-1}$ FLS:L482S, 0.1 mg $mL^{-1}$ NOX, 0.1 mM TPP, 1 mM $Mg^{2+}$, 1 mM DTT, 20% DMSO and 100 mM ethanol at 30 degrees C. 2,3-butanediol production was conducted by reacting 0.5-mL reaction mixture containing 50 mM HEPES buffer solution (pH 8.0), 1 mM $NAD^+$, 1 mM $NADP^+$, 0.1 mg $mL^{-1}$ EtDH:D46G, 0.2 mg $mL^{-1}$ FLS:L482S, 0.1 mg $mL^{-1}$ NOX, 0.1 mg $mL^{-1}$ BDH:S199A, 0.1 mM TPP, 1 mM $Mg^{2+}$, 1 mM DTT, 20% DMSO and 100 mM ethanol at 30 degrees C. 2-butanol production was conducted by reacting 0.5-mL reaction mixture containing 50 mM HEPES buffer (pH 8.0), 1 mM $NAD^+$, 1 mM $NADP^+$, 0.1 mg $mL^{-1}$ EtDH:D46G, 0.2 mg $mL^{-1}$ FLS:L482S, 0.1 mg $mL^{-1}$ NOX, 0.1 mg $mL^{-1}$ BDH:S199A, 0.2 mg $mL^{-1}$ DDH:Q337A/F375I, 0.2 mg $mL^{-1}$ dhaR, 0.1 mM TPP, 1 mM $Mg^{2+}$, 1 mM DTT, 20% DMSO, 1 mM coenzyme $B_{12}$, 100 mM ATP and 100 mM ethanol at 30 degrees C. All reactions were carried out for 6 hours. Each reaction product was identified by gas chromatography. Further, a percentage yield for the product was calculated by a following formula: percentage yield (%)=product yield (mM)/theoretical yield (mM). Theoretically, 2 moles of ethanol may produce 1 mole of acetoin, 2,3-butanediol or 2-butanol.

<1-9> Identification of Recyclability of Cascade Reactions

The purified enzyme was mixed with active silicon oxide particles, and the mixture was cultured for 12 hours at 4 degrees C. Before the immobilization, silicon oxide particles (4830HT; Nanostructured & Amorphous Materials, Houston, Tex., USA) were attached to nano-particles containing glutaraldehyde (Sigma). Thus, the nano-particles were active. The immobilization yield (%) and immobilization efficiency (%) were calculated by the following Equation using a following immobilized enzyme:immobilization efficiency=$(\alpha_i/\alpha_f) \times 100$, immobilization yield=$[\{P_i - (P_w + P_s)\}/P_i] \times 100$. $\alpha_i$ is the total activity level of the immobilized enzyme, $\alpha_f$ is the total activity level of the free enzyme, and $P_i$ is the total protein content of the coenzyme preparation, and $P_w$ and $P_s$ mean a protein concentration of a washing solution or supernatant after immobilization. The acetoin production was conducted by reacting 0.5-mL reaction mixture containing 50 mM HEPES buffer solution (pH 8.0), 1 mM $NAD^+$, 1.06 U $mL^{-1}$ EtDH, 0.05 U $mL^{-1}$ FLS:L482S, 0.98 U $mL^{-1}$ NOX, 0.1 mM TPP, 1 mM $Mg^{2+}$, 1 mM DTT, 20% DMSO and 100 mM ethanol. The 2,3-butanediol production was conducted by reacting 0.5-mL reaction mixture containing 50 mM HEPES buffer solution (pH 8.0), 1 mM $NAD^+$, 1 mM $NADP^+$, 0.1 mg $mL^{-1}$ EtDH:D46G, 0.2 mg $mL^{-1}$ FLS:L482S, 0.1 mg $mL^{-1}$ NOX, 0.1 mg $mL^{-1}$ BDH:S199A, 0.1 mM TPP, 1 mM $Mg^{2+}$, 1 mM DTT, 20% DMSO and 100 mM ethanol at 30 degrees C. for 6 hours. Further, in order to identify the reusability of the immobilized enzyme, the above reaction was performed under the same reaction conditions as above. After each primary reaction cycle, the immobilized enzyme was removed via centrifugation at 4000×g for 30 minutes. The immobilized enzyme was collected and washed with deionized water and a buffer solution. For the secondary reaction cycle, the immobilized enzyme was dissolved in a new buffer solution, and the substrate was added thereto. Then, the reaction was conducted in the same manner as the primary reaction cycle.

<1-10> Analysis Method

For cell growth analysis, cell growth was identified based on a measuring result of the optical density at 600 nm using a spectrophotometer (UV-1800, MAPADA). Protein concentration was measured using the Bradford method. Bovine serum albumin was used as a standard protein. GC-MS analysis was conducted using a gas chromatograph system (Agilent GC9860, Santa Clara, Calif., USA) equipped with a chiral column (Supelco β-DEX™ 120, 30-m length, 0.25-mm inner diameter). The conduction conditions were as follows: $N_2$ was used as a carrier gas at a flow rate of 1.2 mL $min^{-1}$; the injector temperature and detector temperature were set to 215 and 245 degrees C., respectively; the column temperature was maintained at 50 degrees C. for 1.5 minutes, and then increased up to 180 degrees C. at a rate of 15 degrees C. $min^{-1}$.

<Example 2> Identification of Protein Expression of Cascade Enzymes and Variants Thereof in Accordance with Present Disclosure In order to identify the protein expression of the cascade enzymes and its variant protein in accordance with the present disclosure, after induction at 18 degrees C. for 24 hours, cells were obtained via centrifugation and crushed by sonication in an ice bath. The cell lysate was centrifuged for 10 mins at 8000×g to remove cell debris. To obtain NOX, EtDH, FLS, BDH and dhaR enzymes, soluble fractions were purified using HisTrap HP column according to purification protocol (GE Healthcare, Little Chalfont, UK). DDH purification was carried out based on a conventional method [M. Seyfried, et al., J. Bacteriol., 1996, 178, 5793]. Each of the purified enzymes was subjected to ultrafiltration concentrated and desalted, and then detected using SDS-PAGE. As a result, it was identified that the EtDH and EtDH:D46G protein and the BDH and BDH:S199A protein were expressed at the same molecular weight, and the molecular weights of the expressed proteins of wild-type and variant types were the same as each other. Further, it was identified that the NOX proteins derived from *Lactobacillus rhamnosus* and *Lactobacillus brevis* have different molecular weights. Thus, when the same genes are derived from different strains, the proteins expressed therefrom were different from each other. Further, it was identified that the FLS gene was properly expressed.

<Example 3> Identification of $C_4$ Compound Production from Ethanol Using Cascade Enzymes and Variants Thereof in Accordance with Present Disclosure To induce the production of acetoin, 2,3-butanediol and 2-butanol as $C_4$ compounds from ethanol using cascade enzymes and variants thereof in accordance with the present disclosure, the artificial synthetic pathway using the cell-free multi-enzyme catalysis system was designed as shown in FIGS. 1A to 1C. Ethanol was first dehydrogenated by NAD(P)H-dependent EtDH to produce acetaldehyde. The condensation reaction thereof was conducted. Then, using FLS and its variant in accordance with the present disclosure, acetoin was produced. NOX was used to reproduce $NAD^+$. Subsequently, acetoin was reduced by NADPH-dependent BDH to produce 2,3-butanediol. Finally, 2-butanol may be obtained via dehydration and hydrogenation reactions using DDH and BDH, respectively.

<3-1> Identification of Acetoin Production Using FLS Enzyme in Accordance with Present Disclosure In order to identify the ability to convert acetaldehyde to acetoin using the FLS enzyme according to the present disclosure, a VP reaction was performed. Each condition was set as follows: acetaldehyde as a substrate of 50 or 100 nM was treated with FLS enzyme for a treatment time of 0 or 6 hours. As a result, acetoin was produced. When the FLS enzyme was treated and the concentration of acetaldehyde as a substrate varies, the obtained acetoin concentration varies. This was effectively identified based on a color change.

Figure 2:
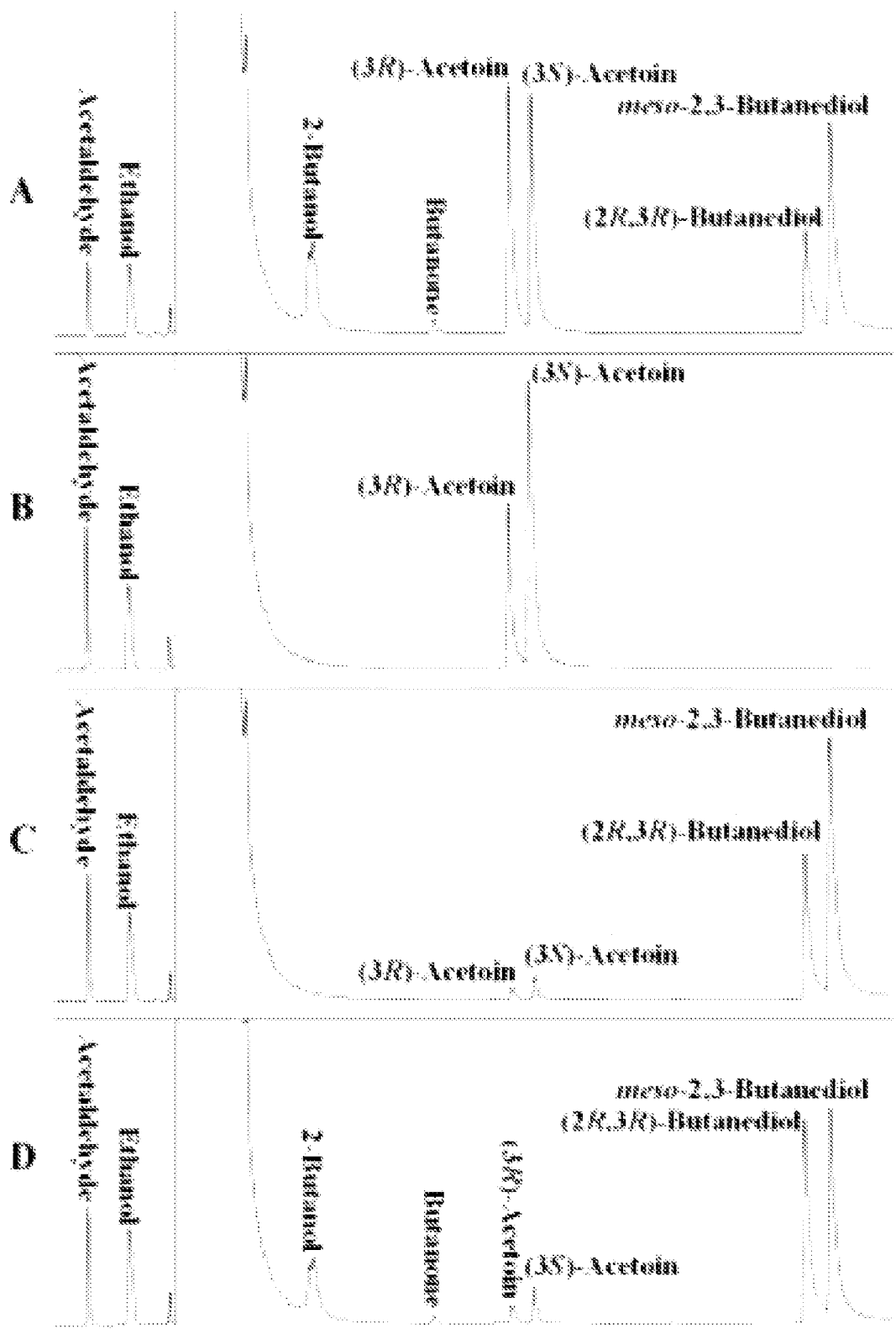
FIG. 2 is a result of chiral-column GC analysis of production of acetoin, 2,3-butanediol and 2-butanol using cascade enzymes and variants thereof in accordance with the present disclosure.

<3-2> Analysis of Acetoin, 2,3-butanediol and 2-butanol Production Using Cascade Enzymes and Variants in Accordance with Present Disclosure Using the cascade enzymes and variants thereof in accordance with the present disclosure, acetoin, 2,3-butanediol and 2-butanol were produced via an artificial synthetic pathway using a cell-free multi-enzyme catalysis system. Thereafter, ethanol, acetaldehyde, and (3 S/3R)-acetoin, (2 S,3 S)-2,3-butanediol, (2R,3R)-2,3-butanediol, meso-2,3-butanediol, butanone and 2-butanol as commercially available standard substances were mixed with each other and the mixture was used as a control. Further, the test results using each cascade enzyme according to cell-free multi-enzyme catalysis in accordance with the present disclosure were analyzed using GC/GC-MS analysis. As a result, it was identified that when using a cell-free multi-enzyme catalysis system using each cascade enzyme in accordance with the present disclosure, acetoin, 2,3-butanediol and 2-butanol of the same peaks as those of the commercially available standard substances were produced (FIG. 2).

<Example 4> Identification of Catalytic Effects of Cascade Enzymes and Variants Thereof in Artificial Synthetic Pathway in Accordance with Present Disclosure <4-1> Comparison of Catalyst Efficiencies Via Measurement of Kinetic Parameters of Cascade Enzymes and Variants Thereof in Accordance with Present Disclosure In order to compare the catalytic efficiencies via measurement of kinetic parameters of cascade enzymes and variants thereof in accordance with the present disclosure, the following experiment was performed. Specifically, the kinetic parameters of EtDH and EtDH:D46G were identified by reacting EtDH and EtDH:D46G with a reaction mixture containing 100 mM glycine-NaOH buffer solution (pH 9.5), 5 mM $Mg^{2+}$, 3 mM $NAD^+/NADP^+$ and 0.5 to 100 mM ethanol at room temperature. The kinetic parameters of FLS and variants thereof were identified by reacting FLS and variants thereof with a reaction mixture containing 100 mM phosphate buffer solution (pH 8.0), 1 mM $Mg^+$, 0.1 mM TPP and 0.5 to 20 mM acetaldehyde at room temperature. The kinetic parameters of BDH and BDH:S199A were identified by reacting BDH and BDH:S199A with a reaction mixture containing 50 mM Tris-HCl buffer solution (pH 7.5), 0.2 mM NADPH, 1 mM DTT; and 0.5 to 100 mM acetoin or 0.5 to 10 mM butanone at room temperature. $K_m$ and $k_{cat}$ values as substrate affinity were identified using nonlinear regression fitting of the Michaelis-Menten equation and the fitting were repeated three times. The test results of DDH and NOX were compared with previous results [(S. Kwak, et al., Bioresource Technol., 2013, 135, 432), and (M. Kopke, et al., Appl. Environ. Microbiol., 2014, 80, 3394)]. Table 5 shows the results. As shown in Table 5, when using ethanol as substrate and using $NAD^+$ as coenzyme, $k_{cat}/K_m$ values of EtDH and EtDH:D46G enzymes were 17.09 and 9.97 $s^{-1}$ $mM^{-1}$, respectively. Thus, it has been identified that using $NAD^+$ as a coenzyme may increase catalyst efficiency rather than using $NADP^+$ as a coenzyme. Further, it was identified that when using acetaldehyde as a substrate and using thiamine pyrophosphate (TPP) as a coenzyme, the $k_{cat}/K_m$ value of the FLS enzyme was $7.69 \times 10^{-3}$ $s^{-1}$ $mM^{-1}$. Further, it was identified that FLS:L482S, FLS:L482R and FLS:L482E as variants thereof had the $k_{cat}/K_m$ values of $1.33 \times 10^{-2}$, $1.06 \times 10^{-2}$ and $9.66 \times 10^{-3}$ $s^{-1}$ $mM^{-1}$, respectively. Thus, it was identified that the catalyst efficiencies thereof were increased by 72.95%, 37.84% and 25.62%, respectively, compared to the wild-type FLS enzyme. Further, it was identified that BDH:S199A enzyme increases catalytic efficiency when using butanone as a substrate and using NADPH as a coenzyme, when compared to wild-type BDH.

TABLE 5

| Enzyme | Substrate/coenzyme | $K_m$ (mM) | $k_{cat}$ ($s^{-1}$) | $k_{cat}/K_m$ ($s^{-1}$ $mM^{-1}$) |
|---|---|---|---|---|
| EtDH | Ethanol/$NAD^+$ | 0.37 ± 0.05 | 6.28 ± 0.11 | 17.09 |
|  | Ethanol/$NADP^+$ | 0 | 0 | 0 |
| EtDH:D46G | Ethanol/$NAD^+$ | 0.57 ± 0.03 | 5.85 ± 0.08 | 9.97 |
|  | Ethanol/$NAD^+$ | 0.60 ± 0.02 | 0.99 ± 0.03 | 1.65 |
| FLS | Acetaldehyde/TPP | 58.46 ± 2.32 | 0.45 ± 0.03 | 7.69 × $10^{-3}$ |
| FLS:L482S | Acetaldehyde/TPP | 47.45 ± 1.26 | 0.63 ± 0.01 | 1.33 × $10^{-2}$ |
| FLS:L482R | Acetaldehyde/TPP | 50.27 ± 1.44 | 0.53 ± 0.02 | 1.06 × $10^{-2}$ |

TABLE 5-continued

| Enzyme | Substrate/coenzyme | $K_m$ (mM) | $k_{cat}$ ($s^{-1}$) | $k_{cat}/K_m$ ($s^{-1}$ $mM^{-1}$) |
|---|---|---|---|---|
| FLS:L482E | Acetaldehyde/TPP | 50.95 ± 1.91 | 0.49 ± 0.03 | 9.66 × $10^{-3}$ |
| BDH | Acetoin/NADPH | 84.56 ± 7.96 | 157.0 ± 9.0 | 18.5 |
|  | Acetoin/NADH | 0 | 0 | 0 |
|  | Butanone/NADPH | 1.94 ± 0.05 | 29.90 ± 1.02 | 15.41 |
|  | Butanone/NADH | 0 | 0 | 0 |
| BDH:S199A | Acetoin/NADPH | 116.1 ± 8.7 | 224.3 ± 9.72 | 19.31 |
|  | Acetoin/NADH | 0 | 0 | 0 |
|  | Butanone/NADPH | 1.08 ± 0.09 | 40.78 ± 1.42 | 37.76 |
|  | Butanone/NADH | 0 | 0 | 0 |
| DDH | 2,3-butanediol/B12 | 10.4 | 35 | 3.4 |
| NOX | O2/NADH | 5.8 × 10−3 | 218.7 | 3.77 × $10^4$ |

<4-2> Identification of Stereoselectivity of Cascade Enzymes and Variants Thereof in Accordance with Present Disclosure To analyze the stereoselectivity of DDH enzyme in accordance with the present disclosure, the whole-cell biocatalytic method was performed using cells (E. coli/pET-DDH-dhaR) expressing DDH enzyme and dhaR as a reactivating factor thereof. The conversion to butanone as a pre-synthesis step of 2-butanol using three 2,3-butanediol isomers (meso-2,3-butanediol, (2R,3R)-butanediol and (2S,3S)-butanediol) as a substrate was identified. As a result, it was identified based on a result of analyzing the stereoselectivity of DDH enzyme in accordance with the present disclosure that 20.56 mM butanone was produced from 50 mM meso-2,3-butanediol. On the other hand, it was identified that when using (2R,3R)-2,3-butanediol and (2S,3S)-2,3-butanediol as a substrate, butanone was not detected. Therefore, DDH enzyme containing dhaR exhibited high catalytic activity for meso-2,3-butanediol in vivo, and thus had excellent stereoselectivity.

<4-3> Identification of Thermal Stability of Cascade Enzymes and Variants Thereof in Accordance with Present Disclosure To identify the thermal stability of the cascade enzymes and variants thereof in accordance with the present disclosure, EtDH (ethanol, $NAD^+$ being contained), EtDH:D46G (ethanol, $NAD^+$ being contained), EtDH:D46G (ethanol, $NADP^+$ being contained), EtDH:D46G (ethanol, $NAD^+$ being contained), FLS (acetaldehyde, TPP being contained), FLS:L482S (acetaldehyde, TPP being contained), BDH:S199A (acetoin, NADPH being contained), BDH:S199A (butanone, NADPH being contained), dhaR-containing DDH:Q337A/F375 (meso-2,3-butanediol, $B_{12}$ being contained), and NOX ($O_2$, NADH being contained) cells were cultured for 6 hours at 30, 37, and 45 degrees C. and then activities thereof were measured. It was identified based on a result of identifying the thermal stability that EtDH, FLS and NOX enzymes exhibited thermal stability of 87.91%, 70.43%, and 91.30%, respectively, at 30 degrees C. Further, it was identified that the NOX enzyme exhibited persistent thermal stability at 37 degrees C. and 45 degrees C.

<Example 5> Acetoin Production Via Artificial Synthetic Pathway in Accordance with Present Disclosure <5-1> Identification of Optimal Reaction Conditions for Conversion from Ethanol to Acetoin For the production of acetoin from ethanol, EtDH, FLS and NOX enzymes were used. Specifically, an initial reaction occurred using 0.5-mL reaction mixture containing 50 mM HEPES buffer (pH 7.0), 0.1 mg $mL^{-1}$ EtDH, 0.2 mg $mL^{-1}$ FLS, 0.1 mg $mL^{-1}$ NOX, 4 mM $NAD^+$, 0.1 mM TPP, 1 mM $Mg^{2+}$, 1 mM DTT, 20% DMSO, and 100 mM ethanol as an initial substrate. The reaction proceeded for 6 hours at 30 degrees C. It was identified that 17.98 mM acetoin was produced from the reaction solution at 35.96% of the theoretical yield. Thus, when using the artificial synthetic pathway in accordance with the present disclosure, the conversion from ethanol to acetoin may be induced. Further, in order to find the optimal reaction conditions in terms of the conditions of temperature, pH, coenzyme ($NAD^+$ and TPP) and metal ions, the temperature was set to 20, 25, 30, 37 and 42 degrees C. Further, pH was set to 6.0, 6.5, 7.0, 7.5, 8.0, 8.5 and 8.5. $NAD^+$ had 1, 2, 4, 6, 8 mM concentrations. TPP had 1, 0.1, 0.2, 0.3, 0.4 and 0.5 mM concentrations. The metal ions employed $Mg^{2+}$, $Mn^{2+}$, $Ca^{2+}$, $Fe^{2+}$, $Ni^{2+}$, $Cu^{2+}$ and $Zn^{2+}$. Optimal reaction conditions were determined from the above various conditions. As a result, it was identified that the most optimal reaction condition was that the pH condition was 8.0, the temperature was 30 degrees C., the concentration of $NAD^+$ was 1 mM, the concentration of TPP was 0.1 mM, and the metal ion was $Mg^{2+}$. It was identified that the reaction flux from ethanol to acetoin was improved when using the most optimal reaction condition. Further, to identify the production of acetoin over time under the optimal reaction condition, EtDH, FLS and NOX enzymes were used, and 100 mM ethanol was used as a substrate and the reaction occurred for 0, 2, 4, 6, and 8 hours. As a result, it was identified that when the reaction time is 6 hours, 22.75 mM acetoin was produced at 45.50% of the theoretical yield.

<5-2> Identification of Rate Limiting Step from Ethanol to Acetoin

To identify the rate limiting step from ethanol to acetoin, each of EtDH, FLS, and NOX enzymes was diluted to a concentration of 1/10, and the concentrations of remaining enzymes other than the diluted one were maintained at a constant concentration. The reaction was repeated three times to identify the amount of acetoin. As a result, it was identified that when the concentration of FLS enzyme was reduced, the production of acetoin was significantly affected, compared to when the EtDH or NOX enzyme was diluted. Therefore, it was identified that the FLS enzyme is an important enzyme for acetoin production.

<5-3> Identification of Catalyst Efficiency of FLS Enzyme Variants and Selection Therefrom To improve the catalyst efficiency of FLS enzyme, mutant hotspots of FLS amino acid sequences were analyzed using the HotSpot Wizard 2.0 server. Site saturation mutagenesis of 6 hot spot residues (T396, T446, M473, 5477, L482 and L499) was identified using the Hot Spot Wizard 2.0 server.

It was identified based on a result of identifying each structural model thereof that 482 sites in FLS played an important role in the enzyme activity. Further, in order to select the FLS variant, FLS and variants thereof L482S, L482R and L482E were subjected to the whole-cell biocatalytic method, while using acetaldehyde (100 mM) as a substrate. The acetoin production concentration was identified using the VP method. Further, the activity (%) of each variant was compared to 0.16 U/mg as the specific activity of FLS after purification. The comparison was repeated three times to obtain an average±standard deviation value. We identified that the FLS variant produced a larger amount of acetoin than the wild-type FLS did. Further, it was identified that the FLS variants L482S, L482R and L482E had activities increased by 59.03%, 36.89% and 34.12%, respectively, compared to the specific activity of the FLS. Therefore, it was identified that L482S among FLS variants was the most effective for acetoin production.

<5-4> Comparison of Structures and Activities of Wild-Type FLS and Variant FLS:L482S Thereof To compare the structures and activities of the wild-type FLS and a variant FLS:L482S thereof, molecular dynamics simulation analysis for 100 ns was used to identify the correlation between structural changes of wild-type FLS and its variant FLS:L482S and the enzyme activity. As a result, we identified that the wild-type FLS and its variant FLS:L482S had the molecular interaction with acetaldehyde as a substrate at the active site residue W480 of the wild-type FLS and its variant FLS:L482S, and the variant FLS:L482S bound more strongly (2.8 Å) to acetaldehyde as a substrate than the wild-type FLS bound (2.1 Å). Further, it was identified that the variant FLS:L482S had hydrogen binding ability higher than that of the wild-type FLS.

<5-5> Comparison of Activity of FLS:L482S Based on Substrate and Concentration

To compare the activity of FLS:L482S according to the concentration of ethanol as a substrate, a 0.5-mL reaction mixture containing 50 mM HEPES buffer (pH 8.0), 1 mM $NAD^+$, 1.06 U $ml^{-1}$ EtDH, 0.05 U $mL^{-1}$ FLS:L482S, 0.98 U $mL^{-1}$ NOX, 0.1 mM TPP, 1 mM $Mg^{2+}$, 1 mM DTT, 20% DMSO, and 100 to 500 mM ethanol reacted. The reaction occurred for 0 to 6 hours at 30 degrees C. Subsequently, acetoin production was identified. As a result, it was identified that when 100 mM ethanol was used as a substrate and the reaction time was 4 hours, 44.39 mM acetoin corresponding to 88.78% of the theoretical yield was obtained. In addition to acetoin, acetaldehyde produced in the metabolism of ethanol was measured. It was found that acetaldehyde concentration increased up to 9.58 mM for 2 hours of reaction and then reduced to 5.65 mM for 6 hours of reaction. Further, it was identified that since no other by-products were accumulated, the artificial synthetic pathway in accordance with the present disclosure for the production of acetoin using FLS:L482S was substrate-specific. Further, it was found based on a result of identifying the effects of substrate concentrations (200, 300, 400 and 500 mM) on the acetoin production, that the production of acetoin and acetaldehyde increased in a concentration-dependent manner.

<Example 6> 2,3-butanediol Production Through Artificial Synthetic Pathway in Accordance with Present Disclosure <6-1> EtDH:D46G Variant and BDH:S199A Preparation When designing the artificial synthetic pathway in accordance with the present disclosure to produce 2,3-butanediol from ethanol, EtDH variants were prepared in order to design NAD(P)H purge valve regulatory node to prevent NADH accumulation while simultaneously using $NAD^+$ and $NADP^+$ as coenzymes to convert ethanol to acetaldehyde. Specifically, the amino acid sequence of EtDH (cnMDH) containing other dehydrogenase was sorted in the PDB database. As a result, a site using only $NAD^+$ as a coenzyme and a site using $NAD^+/NADP^+$ simultaneously were identified. EtDH:D46G containing the site using $NAD^+/NADP^+$ simultaneously was selected. Further, BDH:S199A was prepared by inducing site-specific mutagenesis using a conventional method [D. J. Maddock, et al., Protein Eng. Des. Sel., 2015, 28, 251]. Then, the thermal stability of the variant was analyzed and identified at 30, 37, and 45 degrees C. Thus, it was identified that when EtDH:D46G variant was incubated for 6 hours at 30 degrees C. while acetaldehyde was used as a substrate having coenzymes $NAD^+$ and $NADP^+$, the activity level thereof was maintained at 86.53% and 86.67%. Further, it was identified that when BDH:S199A variant was incubated for 6 hours at 30 degrees C. while NADPH was used as a coenzyme and acetoin was used as a substrate, the activity level of BDH:S199A variant was maintained at 80.81%.

<6-2> Identification of 2,3-butanediol Production from Ethanol Based on Coenzyme To identify 2,3-butanediol production from ethanol based on coenzyme, we reacted EtDH:D46G, FLS:L482S, BDH:S199A and NOX enzymes with 100 mM ethanol in the presence of 1 mM $NAD^+$ and/or 1 mM $NADP^+$. Then, the production concentration (mM) of 2,3-butanediol was identified. As a result, it was identified that 2,3-butanediol was not detected when $NAD^+$ was used as a coenzyme. On the other hand, it was identified that 18.20 mM 2,3-butanediol was produced from ethanol in the presence of $NADP^+$. Therefore, it was identified that as BDH is an NADPH-dependent enzyme that converts acetoin to 2,3-butanediol, the $NADP^+$ coenzyme is required for 2,3-butanediol production.

<6-3> Identification of 2,3-butanediol Production Based on Substrate and Concentration To compare 2,3-butanediol production based on the concentration of ethanol as a substrate, 0.5-mL reaction mixture containing 50 mM HEPES buffer (pH 8.0), 1 mM $NAD^+$, 1 mM $NADP^+$, 0.88 U $mL^{-1}$ EtDH:D46G, 0.05 U $mL^{-1}$ FLS:L482S, 0.98 U $mL^{-1}$ NOX, 5.11 U $mL^{-1}$ BDH:S199A, 0.1 mM TPP, 1 mM $Mg^{2+}$, 1 mM DTT, 20% DMSO and 100 to 500 mM ethanol was subjected to the cell-free multi-enzyme catalysis reaction. The reaction occurred for 0 to 6 hours and at 30 degrees C. Then, 2,3-butanediol production was identified. As a result, it was identified that when using $NAD^+$ and 1 mM $NADP^+$ as coenzymes simultaneously, 88.28% of the theoretical yield of 2,3-butanediol was achieved when the reaction time was 5 hours. Thus, it was identified that NADH accumulation was inhibited, acetoin with low concentration was accumulated in the reaction solution throughout the course of the reaction, and thus, the BDH:S199A exhibited high catalytic efficiency in conversion from acetoin to 2,3-butanediol. As a result, it was identified that when using different substrate concentrations, the production amount of 2,3-butanediol varied depending on the concentration, and when the ethanol concentration was 500 mM, the maximum 2,3-butanediol concentration was 127.3 mM.

<Example 7> Identification of Production of 2-butanol from Ethanol

<7-1> Identification of Conversion of Meso-2,3-butanediol to Butanone According to Reaction Conditions When producing 2-butanol from ethanol, the conversion of meso-2,3-butanediol to butanone according to the reaction conditions was identified. Specifically, 0.2 mg ml$^{-1}$ DDH was used as an enzyme. 0 or 1 mM coenzyme B12, 0 or 100 mM ATP, 0 or 1 mM Mg$^{2+}$ and 0 or 0.2 mg ml$^{-1}$ dhaR as DDH reactivating factor were used. In this connection, the conversion of meso-2,3-butanediol to butanone was identified. As shown in Table 6, it was identified that coenzyme B12 and ATP are required for the catalytic reaction, and dhaR and Mg$^{2+}$ effectively enhanced butanol production from meso-2,3-butanediol. Therefore, it was identified that (2R,3R)-butanediol and (2S,3S)-butanediol were not substrates of DDH, but DDH enzyme catalyzed conversion of only meso-2,3-butanediol to butanone.

TABLE 6

| Reaction | DDH | Coenzyme B12 | ATP | Mg$^{2+}$ | dhaR | Butanone |
| --- | --- | --- | --- | --- | --- | --- |
| A | 0.2 mg ml$^{-1}$ | 0 mM | 0 mM | 0 mM | 0 mg ml$^{-1}$ | 0 ± 0 mM |
| B | 0.2 mg ml$^{-1}$ | 1 mM | 0 mM | 0 mM | 0 mg ml$^{-1}$ | 0 ± 0 mM |
| C | 0.2 mg ml$^{-1}$ | 1 mM | 100 mM | 0 mM | 0 mg ml$^{-1}$ | 1.38 ± 0.12 mM |
| D | 0.2 mg ml$^{-1}$ | 1 mM | 100 mM | 1 mM | 0 mg ml$^{-1}$ | 2.48 ± 0.16 mM |
| E | 0.2 mg ml$^{-1}$ | 1 mM | 100 mM | 1 mM | 0.2 mg ml$^{-1}$ | 5.69 ± 0.21 mM |

<7-2> Identification of 2-butanol Production According to BDH:S199A Variant To identify the production of enantiomers 2-butanol from 2-butanone according to BDH:S199A variant, a whole-cell biocatalytic method was applied to a reaction mixture containing 50 mM HEPES buffer (pH 8.0), 40 g L$^{-1}$ induced *E. coli*/pET28a-BDH:S199A cells (wet cell weight), and 25 mM butanone. The reaction product was analyzed using GC. As a result, it was identified that when using BDH:S199A variant as an enzyme, R-butanol and S-2-butanol were produced at a percentage of 1.23:1.

<7-3> Identification of Forms of Acetoin and 2,3-butanediol

To produce 2-butanol from ethanol, DDH enzyme catalyzes the conversion of not (2R,3R)-butanediol and (2S,3S)-butanediol but only meso-2,3-butanediol to butanone. Thus, the forms of acetoin and 2,3-butanediol produced in the artificial synthetic pathway in accordance with the present disclosure were identified. Specifically, the forms of acetoin and 2,3-butanediol were identified using a GC system equipped with a chiral column. As a result, it was identified that when using acetaldehyde as the substrate and using FLS:L482S variant enzyme, the produced acetoin included (3S)-acetoin and (3R)-acetoin, and thus, meso-2,3-butanediol (65%) and (2R,3R)-butanediol (35%) were produced.

<7-4> Identification of Rate Limiting Step from Ethanol to 2-butanol and Selection of Variant of DDH To identify the rate limiting step from ethanol to 2-butanol, 100 mM was used as the substrate. EtDH:D46G, FLS:L482S, BDH:S199A, DDH containing the reactivating factor dhaR, and NOX were used as enzymes. Specifically, the BDH:S199A or DDH containing the reactivating factor dhaR was diluted to a concentration of 1/10, and the rest of the enzymes other than the diluted one were maintained at a constant concentration and the reaction was repeated 3 times to identify the concentration of 2-butanol (mM). Further, concentrations (mM) of produced butanone when using DDH and S302A, Q337A, F375I, S302A/Q337A, S302A/F375I, Q337A/F375I and S302A/Q337A/F375I as variants thereof were identified. As a result, it was identified that when the concentration of DDH containing the reactivating factor dhaR was lowered, a significant decrease (79.16%) in production concentration of 2-butanol was identified. This confirmed that DDH containing dhaR is an important enzyme for 2-butanol production. Further, it was identified that Q337A/F375I among variants of DDH exhibited the highest butanone production concentration compared to other variants. Further, it was identified based on a result of identifying the protein expression of DDH:Q337A/F375I among the variants of the DDH using SDS-PAGE, that the enzyme containing the DDH reactivating factor dhaR was expressed.

<7-5> Comparison of Structures and Activities of Wild-Type DDH and its Variant DDH:Q337A/F375I To compare the structures and activities of wild-type DDH and its variant DDH:Q337A/F375I, molecular dynamics simulation analysis for 100 ns was used to identify the correlation between structural changes of wild-type DDH and its variant DDH:Q337A/F375I and enzyme activity. As a result, it was identified that the wild-type DDH had molecular interaction with 2,3-butanediol as a substrate at the active site residue E171 of the wild-type DDH, and the wild-type DDH bound (2.6 Å) to the substrate. As a result, it was identified that the variant DDH:Q337A/F375I had the molecular interaction with 2,3-butanediol as a substrate at the active site residue E171 of the variant DDH:Q337A/F375I, and the variant DDH:Q337A/F375I bound (1.9 Å) to the substrate. As a result, it was identified based on a result of 100 ns molecular dynamics analysis, that the active site residue E171 in the wild-type DDH had hydrogen binding and water bridges with the substrate. It was identified that the active site residue E171 in the variant DDH:Q337A/F375I mainly had hydrogen-binding thereto. Therefore, it was identified that the variant DDH:Q337A/F375I bound more strongly to the substrate than the wild-type DDH binds and thus had excellent catalytic activity.

<7-6> Identification of Production of 2-butanol from Ethanol Through Artificial Synthetic Pathway in Accordance with Present Disclosure To identify the final production of 2-butanol from ethanol through the artificial synthetic pathway in accordance with the present disclosure, the cell-free multi-catalyst system was applied to a 0.5-mL reaction mixture containing 50 mM HEPES buffer (pH 8.0), 1 mM NAD$^+$, 1 mM NADP$^+$, 0.88 U mL$^{-1}$ EtDH:D46G, 0.05 U mL$^{-1}$ FLS:L482S, 0.98 U mL$^{-1}$ NOX, 5.11 U mL$^{-1}$ BDH:S199A, 0.01 U mL$^{-1}$ DDH:Q337A/F375I, 0.2 mg mL$^{-1}$ dhaR, 0.1 mM TPP, 1 mM Mg$^{2+}$, 1 mM DTT, 20% DMSO, 1 mM coenzyme B$_{12}$, 100 mM ATP and 0 to 100 mM ethanol at 30 degrees C. and for 6 hours. Thus, production concentrations (mM) of acetaldehyde, acetoin, 2,3-butanediol, 2-butanone and 2-butanol produced from ethanol were identified. As a result, it was identified that 13.62 mM 2-butanol corresponding to 27.24% of theoretical yield was produced. Further, it was identified that the large amount of 2,3-butanediol (up to 32.55 mM) accumulated in the reaction solution, while butanone was not detected during the reaction process.

<Example 8> Identification of Optimal Enzyme in the Artificial Synthetic Pathway in Accordance with Present Disclosure and Specific Activity Level Thereof The optimal enzyme in the artificial synthetic pathway in accordance with the present disclosure, and each of substrate and coenzyme that influences the activity of the optimal enzyme were identified. Further, the specific activity level of each enzyme was identified. As shown in Table 7, it was identified that EtDH or EtDH:D46G variant enzyme had the specific activity level of 10.64±0.15 and 8.81±0.13 U mg$^{-1}$, respectively, when using ethanol as a substrate and using NAD$^+$ as a coenzyme. Further, it was observed that FLS:L482S variant enzyme had the specific activity level of 0.26±0.01 U mg$^{-1}$ when TPP was used as coenzyme and acetaldehyde was used as a substrate. Further, it was observed that the BDH:S199A variant enzyme had the specific activity level of 51.13±3.74 and 57.55±2.65 U mg$^{-1}$, respectively, when using acetoin or butanone as a substrate and using NADPH as a coenzyme. Further, it was observed that DDH:Q337A/F375I variant enzyme containing dhaR had the specific activity level of 0.05±0.01 mg$^{-1}$ when B$_{12}$ coenzyme was used and meso-2,3-butanediol was used as a substrate. Further, it was observed that NOX coenzyme had the specific activity level of 9.83±0.48 mg$^{-1}$ when O$_2$ substrate and NADH coenzyme were used.

TABLE 7

| Enzyme | Substrate/coenzyme | Specific activity (U mg$^{-1}$) |
|---|---|---|
| EtDH | Ethanol/NAD$^+$ | 10.64 ± 0.15 |
| EtDH:D46G | Ethanol/NAD$^+$ | 8.81 ± 0.13 |
|  | Ethanol/NAD$^+$ | 1.35 ± 0.01 |
| FLS:L482S | Acetaldehyde/TPP | 0.26 ± 0.01 |
| BDH:S199A | Acetoin/NADPH | 51.13 ± 3.74 |
|  | Butanone/NADPH | 57.55 ± 2.65 |
| DDH:Q337A/F375I with dhaR | meso-2,3-Butanediol/B12 | 0.05 ± 0.01 |
| NOX | O$_2$/NADH | 9.83 ± 0.48 |

<Example 9> Identification of Recyclability of Cascade Reactions of Enzyme for Acetoin or 2,3-butanediol Production To identify the recyclability of cascade reactions of an enzyme for acetoin or 2,3-butanediol production, according to the method of Example 1-8, each enzyme for acetoin production or each enzyme for 2,3-butanediol production was mixed with active silicon oxide particles. The mixture was incubated for 12 hours and 4 degrees C. Before the immobilization, silicon oxide particles (4830HT; Nanostructured & Amorphous Materials, Houston, Tex., USA) were attached to nano-particles containing glutaraldehyde (Sigma). Thus, the nano-particles were active. The 1st to 10-th reactions were circulated. The immobilization yield (%) and immobilization efficiency (%) were identified. As a result, it was identified that when using an immobilized enzyme, acetoin was effectively produced from ethanol. Further, it was identified based on a result of circulating 1st to 10-th reactions of the immobilized enzyme for acetoin production that 94% efficiency was achieved after the 10-th reuse, compared to the initial 1st acetoin production concentration. Further, it was identified that 2,3-butanediol was effectively produced from ethanol when an immobilized enzyme is used. Further, it was identified based on a result of circulating 1st to 10-th reactions of the immobilized enzyme for 2,3-butanediol production that 73% efficiency was achieved after the 10-th reuse, compared to the initial 1st 2,3-butanediol production concentration.

The invention claimed is:

1. A FLS (formolase) variant selected from the group consisting of:
   a variant in which 482-th leucine in FLS represented by SEQ ID NO: 8 is substituted with serine;
   a variant in which 482-th leucine in FLS represented by SEQ ID NO: 8 is substituted with arginine; and
   a variant in which 482-th leucine in FLS represented by SEQ ID NO: 8 is substituted with glutamic acid.

2. The FLS variant of claim 1, wherein the variant (FLS:L482S) in which 482-th leucine in the FLS is substituted with serine is represented by an amino acid of SEQ ID NO: 10,
   wherein the variant (FLS:L482R) in which 482-th leucine in the FLS is substituted with arginine is represented by an amino acid of SEQ ID NO: 11,
   wherein the variant (FLS:L482E) in which 482-th leucine in the FLS is substituted with glutamic acid is represented by an amino acid of SEQ ID NO: 12.

* * * * *

SEQUENCE LISTING

<160> NUMBER OF SEQ ID NOS: 46

<210> SEQ ID NO 1
<211> LENGTH: 1362
<212> TYPE: DNA
<213> ORGANISM: Artificial Sequence
<220> FEATURE:
<223> OTHER INFORMATION: Full-length NOX

<400> SEQUENCE: 1

```
atgaagattc ttgtcattgg tgctacccat gccggtacat ttgcaaccca gcagatccta      60
accgaccatc cagatgcaga ggttactgtc tacgaacgca ataacaacct gtccttcctc     120
tcgtgcggca ttgccttgtg ggttggtgat catgtcagtg acccggataa aatgttctat     180
tccagtcccg aagcactcgc taaactcggt gctaatatgc aaatggaaca tgatgtgctc     240
aatattgatc cagcaactaa aacagttgaa gtcaaggatc taaaaaccgg aaccgttact     300
accgatactt atgacaaatt agtctacaca accggatcga cgccaatcat tccaaatatt     360
```

```
cccggtatcc acgattcaaa cgtctactta tgcaaaaatt ggtccgacgc caagacgcta    420
aaagatctgg ccccgtccat taaaagcgcc attgtcatcg gtgcaggcta catcggtgca    480
gaattagccg aacaatttgc gttaaccgac aaagaagtca cgttaatcga tggacttcca    540
cgggttttgg cgaaaaactt tgacgccact atcacggatc gcgttgaaaa gctttacacc    600
gatcacgggg ttcacttggc actcaatgag atggttaccg agttcgcaca agctgatcag    660
ggtatcaagg ttacaaccaa taaggcgac tataccgcgg atattgcaat tttatgtacc     720
ggcttccgtc cgaacacgga tctgctaaag gaccatctgg acaccctgcc taatggcgct    780
gtcataacaa atgcatatat gcagaccagt gaccccgaca ttttcgctgc tggtgatacc    840
gctaccgtcc actataatcc gactggcaaa aatgactaca tcccgcttgc gaccaacgca    900
gtccgtcaag gcattcttgt tggtaaaaat atcatgaccc ccacggaaaa atacctggga    960
acacaatcta gctcggccgt tgaactttt gatcacgcca ttgcggcaag cggcctaacg    1020
gtggaaggcg ctcacacacg tggacttgag cttgatagtg tcacgatcga acaggattat   1080
cgccccgatt tcatgttaac cacaacgccg gtgctctgca gcctgacatg ggatcccaag   1140
acgcatgaag ttaaaggagg tgccttttc tccaagcacg atatcagcca aagcgctaat    1200
gtcatttcgc ttgcgatcca gacccacatg acgatcgaaa cacttgcgat ggttgacatg   1260
ctcttccaac ctaacttcga tcagccgatt aactgggtaa atgccgtggc tatggcggca   1320
gttgacaagg ctaaaagaa gccgacaaca ccggtagcct aa                       1362
```

<210> SEQ ID NO 2
<211> LENGTH: 453
<212> TYPE: PRT
<213> ORGANISM: Artificial Sequence
<220> FEATURE:
<223> OTHER INFORMATION: AMINO ACID OF NOX

<400> SEQUENCE: 2

```
Met Lys Ile Leu Val Ile Gly Ala Thr His Ala Gly Thr Phe Ala Thr
1               5                   10                  15

Gln Gln Ile Leu Thr Asp His Pro Asp Ala Glu Val Thr Val Tyr Glu
                20                  25                  30

Arg Asn Asn Asn Leu Ser Phe Leu Ser Cys Gly Ile Ala Leu Trp Val
            35                  40                  45

Gly Asp His Val Ser Asp Pro Asp Lys Met Phe Tyr Ser Ser Pro Glu
        50                  55                  60

Ala Leu Ala Lys Leu Gly Ala Asn Met Gln Met Glu His Asp Val Leu
65                  70                  75                  80

Asn Ile Asp Pro Ala Thr Lys Thr Val Glu Val Lys Asp Leu Lys Thr
                85                  90                  95

Gly Thr Val Thr Thr Asp Thr Tyr Asp Lys Leu Val Tyr Thr Thr Gly
            100                 105                 110

Ser Thr Pro Ile Ile Pro Asn Ile Pro Gly Ile His Asp Ser Asn Val
        115                 120                 125

Tyr Leu Cys Lys Asn Trp Ser Asp Ala Lys Thr Leu Lys Asp Leu Ala
    130                 135                 140

Pro Ser Ile Lys Ser Ala Ile Val Ile Gly Ala Gly Tyr Ile Gly Ala
145                 150                 155                 160

Glu Leu Ala Glu Gln Phe Ala Leu Thr Asp Lys Glu Val Thr Leu Ile
                165                 170                 175

Asp Gly Leu Pro Arg Val Leu Ala Lys Asn Phe Asp Ala Thr Ile Thr
            180                 185                 190
```

Asp Arg Val Glu Lys Leu Tyr Thr Asp His Gly Val His Leu Ala Leu
    195                 200                 205

Asn Glu Met Val Thr Glu Phe Ala Gln Ala Asp Gln Gly Ile Lys Val
210                 215                 220

Thr Thr Asn Lys Gly Asp Tyr Thr Ala Asp Ile Ala Ile Leu Cys Thr
225                 230                 235                 240

Gly Phe Arg Pro Asn Thr Asp Leu Leu Lys Asp His Leu Asp Thr Leu
            245                 250                 255

Pro Asn Gly Ala Val Ile Thr Asn Ala Tyr Met Gln Thr Ser Asp Pro
            260                 265                 270

Asp Ile Phe Ala Ala Gly Asp Thr Ala Thr Val His Tyr Asn Pro Thr
        275                 280                 285

Gly Lys Asn Asp Tyr Ile Pro Leu Ala Thr Asn Ala Val Arg Gln Gly
    290                 295                 300

Ile Leu Val Gly Lys Asn Ile Met Thr Pro Thr Glu Lys Tyr Leu Gly
305                 310                 315                 320

Thr Gln Ser Ser Ser Ala Val Glu Leu Phe Asp His Ala Ile Ala Ala
            325                 330                 335

Ser Gly Leu Thr Val Glu Gly Ala His Thr Arg Gly Leu Glu Leu Asp
            340                 345                 350

Ser Val Thr Ile Glu Gln Asp Tyr Arg Pro Asp Phe Met Leu Thr Thr
        355                 360                 365

Thr Pro Val Leu Cys Ser Leu Thr Trp Asp Pro Lys Thr His Glu Val
370                 375                 380

Lys Gly Gly Ala Phe Phe Ser Lys His Asp Ile Ser Gln Ser Ala Asn
385                 390                 395                 400

Val Ile Ser Leu Ala Ile Gln Thr His Met Thr Ile Glu Thr Leu Ala
            405                 410                 415

Met Val Asp Met Leu Phe Gln Pro Asn Phe Asp Gln Pro Ile Asn Trp
            420                 425                 430

Val Asn Ala Val Ala Met Ala Ala Val Asp Lys Ala Lys Lys Lys Pro
        435                 440                 445

Thr Thr Pro Val Ala
    450

<210> SEQ ID NO 3
<211> LENGTH: 1173
<212> TYPE: DNA
<213> ORGANISM: Artificial Sequence
<220> FEATURE:
<223> OTHER INFORMATION: Full-length EtDH

<400> SEQUENCE: 3
atgacccatc tgaatattgc taatcgcgtg gatagttttt ttattccgtg tgttaccctg      60
tttggcccgg gttgcgcacg tgaaaccggc gcccgtgcac gtagtctggg cgcacgtaaa    120
gccctgattg ttaccgatgc tggcctgcat aaaatgggcc tgtcagaagt tgttgcaggt    180
catattcgtg aagctggtct gcaagcagtg attttttccgg cgctgaaacc gaatccgacc    240
gatgttaatg tgcatgatgg tgtgaaactg tttgaacgtg aagaatgtga ttttattgtg    300
tctctgggtg cggtagcag ccatgattgc gctaaaggca ttggcctggt taccgcgggt    360
ggcggccata ttcgcgatta tgaaggtatt gataaaagta ccgtgccgat gaccccgctg    420
atttcaatta ataccaccgc tggtacagcc gccgaaatga cccgcttttg tattattacc    480
aattctagta atcatgttaa atggcaattg ttgattggc gttgcacccc gctgattgcg    540

```
attgatgacc ctagtctgat ggtggcaatg ccgccggcgc tgaccgcggc aaccggcatg        600
gatgctctga cccatgcaat tgaagcgtat gtgtcaaccg cagccacccc gattaccgat        660
gcgtgtgcag aaaaagcgat tgtgctgatt gcggaatggc tgccgaaagc ggttgcgaat        720
ggcgatagca tggaagcccg tgcggctatg tgctatgcac agtatctggc aggcatggcg        780
tttaataatg catcactggg ttatgtgcac gctatggcac atcagctggg cggcttttat        840
aatctgccgc atggtgtgtg caatgcaatt ctgctgccgc atgtgtcaga atttaatctg        900
attgccgcac cggaacgcta tgcacgcatt gccgaactgc tgggtgaaaa tattggtggt        960
ctgtctgctc atgatgcggc gaaagctgct gttagcgcga ttcgcaccct gtctacctct       1020
attggtattc cggctggtct ggcgggtctg ggtgttaaag ccgatgacca tgaagttatg       1080
gccagcaatg ctcagaaaga tgcttgtatg ctgaccaatc cgcgcaaagc caccctggcc       1140
caggttatgg cgattttttgc tgccgccatg taa                                    1173
```

<210> SEQ ID NO 4
<211> LENGTH: 390
<212> TYPE: PRT
<213> ORGANISM: Artificial Sequence
<220> FEATURE:
<223> OTHER INFORMATION: AMINO ACID OF EtDH

<400> SEQUENCE: 4

```
Met Thr His Leu Asn Ile Ala Asn Arg Val Asp Ser Phe Phe Ile Pro
1               5                   10                  15

Cys Val Thr Leu Phe Gly Pro Gly Cys Ala Arg Glu Thr Gly Ala Arg
            20                  25                  30

Ala Arg Ser Leu Gly Ala Arg Lys Ala Leu Ile Val Thr Asp Ala Gly
        35                  40                  45

Leu His Lys Met Gly Leu Ser Glu Val Val Ala Gly His Ile Arg Glu
    50                  55                  60

Ala Gly Leu Gln Ala Val Ile Phe Pro Gly Ala Glu Pro Asn Pro Thr
65                  70                  75                  80

Asp Val Asn Val His Asp Gly Val Lys Leu Phe Glu Arg Glu Cys
                85                  90                  95

Asp Phe Ile Val Ser Leu Gly Gly Gly Ser Ser His Asp Cys Ala Lys
            100                 105                 110

Gly Ile Gly Leu Val Thr Ala Gly Gly His Ile Arg Asp Tyr Glu
        115                 120                 125

Gly Ile Asp Lys Ser Thr Val Pro Met Thr Pro Leu Ile Ser Ile Asn
    130                 135                 140

Thr Thr Ala Gly Thr Ala Ala Glu Met Thr Arg Phe Cys Ile Ile Thr
145                 150                 155                 160

Asn Ser Ser Asn His Val Lys Met Ala Ile Val Asp Trp Arg Cys Thr
                165                 170                 175

Pro Leu Ile Ala Ile Asp Asp Pro Ser Leu Met Val Ala Met Pro Pro
            180                 185                 190

Ala Leu Thr Ala Ala Thr Gly Met Asp Ala Leu Thr His Ala Ile Glu
        195                 200                 205

Ala Tyr Val Ser Thr Ala Thr Pro Ile Thr Asp Ala Cys Ala Glu
    210                 215                 220

Lys Ala Ile Val Leu Ile Ala Glu Trp Leu Pro Lys Ala Val Ala Asn
225                 230                 235                 240

Gly Asp Ser Met Glu Ala Arg Ala Ala Met Cys Tyr Ala Gln Tyr Leu
```

```
                  245                 250                 255
Ala Gly Met Ala Phe Asn Asn Ala Ser Leu Gly Tyr Val His Ala Met
            260                 265                 270

Ala His Gln Leu Gly Gly Phe Tyr Asn Leu Pro His Gly Val Cys Asn
        275                 280                 285

Ala Ile Leu Leu Pro His Val Ser Glu Phe Asn Leu Ile Ala Ala Pro
    290                 295                 300

Glu Arg Tyr Ala Arg Ile Ala Glu Leu Leu Gly Glu Asn Ile Gly Gly
305                 310                 315                 320

Leu Ser Ala His Asp Ala Ala Lys Ala Ala Val Ser Ala Ile Arg Thr
                325                 330                 335

Leu Ser Thr Ser Ile Gly Ile Pro Ala Gly Leu Ala Gly Leu Gly Val
            340                 345                 350

Lys Ala Asp Asp His Glu Val Met Ala Ser Asn Ala Gln Lys Asp Ala
        355                 360                 365

Cys Met Leu Thr Asn Pro Arg Lys Ala Thr Leu Ala Gln Val Met Ala
    370                 375                 380

Ile Phe Ala Ala Ala Met
385                 390

<210> SEQ ID NO 5
<211> LENGTH: 1173
<212> TYPE: DNA
<213> ORGANISM: Artificial Sequence
<220> FEATURE:
<223> OTHER INFORMATION: EtDH:D46G

<400> SEQUENCE: 5
atgacccatc tgaatattgc taatcgcgtg gatagttttt ttattccgtg tgttaccctg      60
tttggcccgg gttgcgcacg tgaaaccggc gcccgtgcac gtagtctggg cgcacgtaaa     120
gccctgattg ttaccggtgc tggcctgcat aaaatgggcc tgtcagaagt tgttgcaggt     180
catattcgtg aagctggtct gcaagcagtg attttccgg gcgctgaacc gaatccgacc      240
gatgttaatg tgcatgatgg tgtgaaactg tttgaacgtg aagaatgtga tttattgtg      300
tctctgggtg gcggtagcag ccatgattgc gctaaaggca ttggcctggt taccgcgggt     360
ggcggccata ttcgcgatta tgaaggtatt gataaaagta ccgtgccgat gaccccgctg     420
atttcaatta ataccaccgc tggtacagcc gccgaaatga cccgcttttg tattattacc     480
aattctagta tcatgttaa aatggcaatt gttgattggc gttgcacccc gctgattgcg      540
attgatgacc ctagtctgat ggtggcaatg ccgccggcgc tgaccgcggc aaccggcatg     600
gatgctctga cccatgcaat tgaagcgtat gtgtcaaccg cagccacccc gattaccgat     660
gcgtgtgcag aaaagcgat tgtgctgatt gcggaatggc tgccgaaagc ggttgcgaat      720
ggcgatagca tggaagcccg tgcggctatg tgctatgcac agtatctggc aggcatggcg     780
tttaataatg catcactggg ttatgtgcac gctatggcac atcagctggg cggcttttat     840
aatctgccgc atggtgtgtg caatgcaatt ctgctgccgc atgtgtcaga atttaatctg     900
attgccgcac cggaacgcta tgcacgcatt gccgaactgc tgggtgaaaa tattggtggt     960
ctgtctgctc atgatgcggc gaaagctgct gttagcgcga ttcgcaccct gtctacctct    1020
attggtattc cggctggtct ggcgggtctg ggtgttaaag ccgatgacca tgaagttatg    1080
gccagcaatg ctcagaaaga tgcttgtatg ctgaccaatc cgcgcaaagc caccctggcc    1140
caggttatgg cgattttgc tgccgccatg taa                                  1173
```

<210> SEQ ID NO 6
<211> LENGTH: 390
<212> TYPE: PRT
<213> ORGANISM: Artificial Sequence
<220> FEATURE:
<223> OTHER INFORMATION: AMINO ACID OF EtDH:D46G

<400> SEQUENCE: 6

```
Met Thr His Leu Asn Ile Ala Asn Arg Val Asp Ser Phe Phe Ile Pro
 1               5                  10                  15

Cys Val Thr Leu Phe Gly Pro Gly Cys Ala Arg Glu Thr Gly Ala Arg
            20                  25                  30

Ala Arg Ser Leu Gly Ala Arg Lys Ala Leu Ile Val Thr Gly Ala Gly
        35                  40                  45

Leu His Lys Met Gly Leu Ser Glu Val Val Ala Gly His Ile Arg Glu
    50                  55                  60

Ala Gly Leu Gln Ala Val Ile Phe Pro Gly Ala Glu Pro Asn Pro Thr
65                  70                  75                  80

Asp Val Asn Val His Asp Gly Val Lys Leu Phe Arg Glu Glu Cys
                85                  90                  95

Asp Phe Ile Val Ser Leu Gly Gly Gly Ser His Asp Cys Ala Lys
            100                 105                 110

Gly Ile Gly Leu Val Thr Ala Gly Gly His Ile Arg Asp Tyr Glu
        115                 120                 125

Gly Ile Asp Lys Ser Thr Val Pro Met Thr Pro Leu Ile Ser Ile Asn
    130                 135                 140

Thr Thr Ala Gly Thr Ala Ala Glu Met Thr Arg Phe Cys Ile Ile Thr
145                 150                 155                 160

Asn Ser Ser Asn His Val Lys Met Ala Ile Val Asp Trp Arg Cys Thr
                165                 170                 175

Pro Leu Ile Ala Ile Asp Asp Pro Ser Leu Met Val Ala Met Pro Pro
            180                 185                 190

Ala Leu Thr Ala Ala Thr Gly Met Asp Ala Leu Thr His Ala Ile Glu
        195                 200                 205

Ala Tyr Val Ser Thr Ala Ala Thr Pro Ile Thr Asp Ala Cys Ala Glu
    210                 215                 220

Lys Ala Ile Val Leu Ile Ala Glu Trp Leu Pro Lys Ala Val Ala Asn
225                 230                 235                 240

Gly Asp Ser Met Glu Ala Arg Ala Ala Met Cys Tyr Ala Gln Tyr Leu
                245                 250                 255

Ala Gly Met Ala Phe Asn Asn Ala Ser Leu Gly Tyr Val His Ala Met
            260                 265                 270

Ala His Gln Leu Gly Gly Phe Tyr Asn Leu Pro His Gly Val Cys Asn
        275                 280                 285

Ala Ile Leu Leu Pro His Val Ser Glu Phe Asn Leu Ile Ala Ala Pro
    290                 295                 300

Glu Arg Tyr Ala Arg Ile Ala Glu Leu Leu Gly Glu Asn Ile Gly Gly
305                 310                 315                 320

Leu Ser Ala His Asp Ala Ala Lys Ala Ala Val Ser Ala Ile Arg Thr
                325                 330                 335

Leu Ser Thr Ser Ile Gly Ile Pro Ala Gly Leu Ala Gly Leu Gly Val
            340                 345                 350

Lys Ala Asp Asp His Glu Val Met Ala Ser Asn Ala Gln Lys Asp Ala
        355                 360                 365
```

| Cys | Met | Leu | Thr | Asn | Pro | Arg | Lys | Ala | Thr | Leu | Ala | Gln | Val | Met | Ala |
|-----|-----|-----|-----|-----|-----|-----|-----|-----|-----|-----|-----|-----|-----|-----|-----|
| 370 |     |     |     |     | 375 |     |     |     |     | 380 |     |     |     |     |     |

| Ile | Phe | Ala | Ala | Ala | Met |
|-----|-----|-----|-----|-----|-----|
| 385 |     |     |     |     | 390 |

<210> SEQ ID NO 7
<211> LENGTH: 1692
<212> TYPE: DNA
<213> ORGANISM: Artificial Sequence
<220> FEATURE:
<223> OTHER INFORMATION: Full-length FLS

<400> SEQUENCE: 7

```
atggcgatga ttacaggcgg cgaactggtt gttcgcaccc taataaaggc tggggtcgaa      60
catctgttcg gcctgcacgg cattcatatc gatacgattt tcaagcctg tctcgatcat     120
gatgtgccga tcatcgacac ccgccatgag ccgccgcag gcatgcggc cgagggctat      180
gcccgcgctg cgccaagct gggcgtggcg ctggtcacgg cgggcggggg atttaccaat      240
gcggtcacgc ccattgccaa cgctcgtacc gatcgcacgc cggtgctctt cctcaccgga     300
tcgggcgcgc tgcgtgatga tgaaaccaac acgttgcagg cggggattga tcaggtcgcc     360
atggcggcgc ccattaccaa atgggcgcat cgggtgatgg caaccgagca tatcccacgg     420
ctggtgatgc aggcgatccg cgccgcgttg agcgcgccac gcgggccggt gttgctggat     480
ctgccgtggg atattctgat gaaccagatt gatgaggata cgtcattat ccccgatctg      540
gtcttgtccg cgcatggggc ccatcccgac cctgccgatc tggatcaggc tctcgcgctt     600
ttgcgcaagg cggagcggcc ggtcatcgtg ctcggctcag aagcctcgcg dacagcgcgc     660
aagacggcgc ttagcgcctt cgtggcggcg actggcgtgc cggtgtttgc cgattatgaa     720
gggctaagca tgctctcggg gctgcccgat gctatgcggg gcgggctggt gcaaaacctc     780
tattcttttg ccaaagccga tgccgcgcca gatctcgtgc tgatgctggg ggcgcgcttt     840
ggccttaaca ccgggcatgg atctgggcag ttgatcccc atagcgcgca ggtcattcag     900
gtcgaccctg atgcctgcga gctgggacgc ctgcagggca tcgctctggg cattgtggcc     960
gatgtgggtg ggaccatcga ggctttggcg caggccaccg cgcaagatgc ggcttggccg    1020
gatcgcggcg actggtgcgc caaagtgacg gatctggcgc aagagcgcta tgccagcatc    1080
gctgcgaaat cgagcagcga gcatgcgctc caccccttc acgcctcgca ggtcattgcc    1140
aaacacgtcg atgcaggggt gacggtggta gcggatggtg gcctgaccta tctctggctg    1200
tccgaagtga tgagccgcgt gaaacccggc ggttttctct gccacggcta tctaaactcg    1260
atgggcgtgg gcttcggcac ggcgctgggc gcgcaagtgg ccgatcttga agcaggccgc    1320
cgcacgatcc ttgtgaccgg cgatggctcg gtgggctata gcatcggtga atttgatacg    1380
ctggtgcgca acaattgcc gctgatcgtc atcatcatga caaccaaag ctgggggtgg     1440
acattgcatt ccagcaatt ggccgtcggc cccaatcgcg tgacgggcac ccgtttggaa    1500
aatggctcct atcacgggt ggccgccgcc tttggcgcgg atggctatca tgtcgacagt    1560
gtggagagct ttctgcggc tctggcccaa gcgctcgccc ataatcgccc cgcctgcatc    1620
aatgtcgcgg tcgcgctcga tccgatcccg cccgaagaac tcattctgat cggcatggac    1680
cccttcgcat ga                                                        1692
```

<210> SEQ ID NO 8
<211> LENGTH: 563
<212> TYPE: PRT
<213> ORGANISM: Artificial Sequence
<220> FEATURE:
<223> OTHER INFORMATION: amino acid of Full-length FLS

<400> SEQUENCE: 8

```
Met Ala Met Ile Thr Gly Gly Glu Leu Val Val Arg Thr Leu Ile Lys
1               5                   10                  15

Ala Gly Val Glu His Leu Phe Gly Leu His Gly Ile His Ile Asp Thr
            20                  25                  30

Ile Phe Gln Ala Cys Leu Asp His Asp Val Pro Ile Ile Asp Thr Arg
        35                  40                  45

His Glu Ala Ala Gly His Ala Ala Glu Gly Tyr Ala Arg Ala Gly
    50                  55                  60

Ala Lys Leu Gly Val Ala Leu Val Thr Ala Gly Gly Phe Thr Asn
65              70                  75                  80

Ala Val Thr Pro Ile Ala Asn Ala Arg Thr Asp Arg Thr Pro Val Leu
            85                  90                  95

Phe Leu Thr Gly Ser Gly Ala Leu Arg Asp Asp Glu Thr Asn Thr Leu
        100                 105                 110

Gln Ala Gly Ile Asp Gln Val Ala Met Ala Ala Pro Ile Thr Lys Trp
    115                 120                 125

Ala His Arg Val Met Ala Thr Glu His Ile Pro Arg Leu Val Met Gln
130                 135                 140

Ala Ile Arg Ala Ala Leu Ser Ala Pro Arg Gly Pro Val Leu Leu Asp
145                 150                 155                 160

Leu Pro Trp Asp Ile Leu Met Asn Gln Ile Asp Glu Asp Ser Val Ile
                165                 170                 175

Ile Pro Asp Leu Val Leu Ser Ala His Gly Ala His Pro Asp Pro Ala
            180                 185                 190

Asp Leu Asp Gln Ala Leu Ala Leu Leu Arg Lys Ala Glu Arg Pro Val
        195                 200                 205

Ile Val Leu Gly Ser Glu Ala Ser Arg Thr Ala Arg Lys Thr Ala Leu
    210                 215                 220

Ser Ala Phe Val Ala Ala Thr Gly Val Pro Val Phe Ala Asp Tyr Glu
225                 230                 235                 240

Gly Leu Ser Met Leu Ser Gly Leu Pro Asp Ala Met Arg Gly Gly Leu
                245                 250                 255

Val Gln Asn Leu Tyr Ser Phe Ala Lys Ala Asp Ala Ala Pro Asp Leu
            260                 265                 270

Val Leu Met Leu Gly Ala Arg Phe Gly Leu Asn Thr Gly His Gly Ser
        275                 280                 285

Gly Gln Leu Ile Pro His Ser Ala Gln Val Ile Gln Val Asp Pro Asp
    290                 295                 300

Ala Cys Glu Leu Gly Arg Leu Gln Gly Ile Ala Leu Gly Ile Val Ala
305                 310                 315                 320

Asp Val Gly Gly Thr Ile Glu Ala Leu Ala Gln Ala Thr Ala Gln Asp
                325                 330                 335

Ala Ala Trp Pro Asp Arg Gly Asp Trp Cys Ala Lys Val Thr Asp Leu
            340                 345                 350

Ala Gln Glu Arg Tyr Ala Ser Ile Ala Ala Lys Ser Ser Glu His
        355                 360                 365

Ala Leu His Pro Phe His Ala Ser Gln Val Ile Ala Lys His Val Asp
    370                 375                 380

Ala Gly Val Thr Val Val Ala Asp Gly Gly Leu Thr Tyr Leu Trp Leu
385                 390                 395                 400
```

```
Ser Glu Val Met Ser Arg Val Lys Pro Gly Gly Phe Leu Cys His Gly
            405                 410                 415

Tyr Leu Asn Ser Met Gly Val Gly Phe Gly Thr Ala Leu Gly Ala Gln
            420                 425                 430

Val Ala Asp Leu Glu Ala Gly Arg Arg Thr Ile Leu Val Thr Gly Asp
            435                 440                 445

Gly Ser Val Gly Tyr Ser Ile Gly Glu Phe Asp Thr Leu Val Arg Lys
            450                 455                 460

Gln Leu Pro Leu Ile Val Ile Ile Met Asn Asn Gln Ser Trp Gly Trp
465                 470                 475                 480

Thr Leu His Phe Gln Gln Leu Ala Val Gly Pro Asn Arg Val Thr Gly
            485                 490                 495

Thr Arg Leu Glu Asn Gly Ser Tyr His Gly Val Ala Ala Ala Phe Gly
            500                 505                 510

Ala Asp Gly Tyr His Val Asp Ser Val Glu Ser Phe Ser Ala Ala Leu
            515                 520                 525

Ala Gln Ala Leu Ala His Asn Arg Pro Ala Cys Ile Asn Val Ala Val
            530                 535                 540

Ala Leu Asp Pro Ile Pro Pro Glu Glu Leu Ile Leu Ile Gly Met Asp
545                 550                 555                 560

Pro Phe Ala

<210> SEQ ID NO 9
<211> LENGTH: 1692
<212> TYPE: DNA
<213> ORGANISM: Artificial Sequence
<220> FEATURE:
<223> OTHER INFORMATION: FLS:L482S

<400> SEQUENCE: 9
atggcgatga ttacaggcgg cgaactggtt gttcgcaccc taataaaggc tggggtcgaa      60
catctgttcg gcctgcacgg cattcatatc gatacgattt tcaagcctg tctcgatcat     120
gatgtgccga tcatcgacac ccgccatgag gccgccgcag gcatgcggc cgagggctat     180
gcccgcgctg gcgccaagct gggcgtggcg ctggtcacgg cgggcggggg atttaccaat     240
gcggtcacgc ccattgccaa cgctcgtacc gatcgcacgc cggtgctctt cctcaccgga     300
tcgggcgcgc tgcgtgatga tgaaaccaac acgttgcagg cggggattga tcaggtcgcc     360
atggcggcgc ccattaccaa atgggcgcat cgggtgatgg caaccgagca tatcccacgg     420
ctggtgatgc aggcgatccg cgccgcgttg agcgcgccac gcgggccggt gttgctggat     480
ctgccgtggg atattctgat gaaccagatt gatgaggata gcgtcattat ccccgatctg     540
gtcttgtccg cgcatggggc ccatcccgac cctgccgatc tggatcaggc tctcgcgctt     600
ttgcgcaagg cggagcggcc ggtcatcgtg ctcggctcag aagcctcgcg gacagcgcgc     660
aagacggcgc ttagcgcctt cgtggcggcg actggcgtgc cggtgtttgc cgattatgaa     720
gggctaagca tgctctcggg gctgcccgat gctatgcggg cgggctggt gcaaaacctc     780
tattcttttg ccaaagccga tgccgcgcca gatctcgtgc tgatgctggg ggcgcgcttt     840
ggccttaaca ccgggcatgg atctgggcag ttgatccccc atagcgcgca ggtcattcag     900
gtcgaccctg atgcctgcga gctgggacgc tgcagggca tcgctctggg cattgtggcc     960
gatgtgggtg ggaccatcga ggctttggcg caggccaccg cgcaagatgc ggcttggccg    1020
gatcgcggcg actggtgcgc caaagtgacg gatctggcgc aagagcgcta tgccagcatc    1080
```

```
gctgcgaaat cgagcagcga gcatgcgctc caccccttc acgcctcgca ggtcattgcc    1140
aaacacgtcg atgcaggggt gacggtggta gcggatggtg gcctgaccta tctctggctg    1200
tccgaagtga tgagccgcgt gaaacccggc ggttttctct gccacggcta tctaaactcg    1260
atgggcgtgg gcttcggcac ggcgctgggc gcgcaagtgg ccgatcttga agcaggccgc    1320
cgcacgatcc ttgtgaccgg cgatggctcg gtgggctata gcatcggtga atttgatacg    1380
ctggtgcgca acaattgcc gctgatcgtc atcatcatga acaaccaaag ctggggtgg     1440
acaagtcatt ccagcaatt ggccgtcggc cccaatcgcg tgacgggcac ccgtttggaa    1500
aatggctcct atcacgggt ggccgccgcc tttggcgcgg atggctatca tgtcgacagt    1560
gtggagagct tttctgcggc tctggcccaa cgctcgccc ataatcgccc cgcctgcatc    1620
aatgtcgcgg tcgcgctcga tccgatcccg cccgaagaac tcattctgat cggcatggac    1680
cccttcgcat ga                                                       1692

<210> SEQ ID NO 10
<211> LENGTH: 563
<212> TYPE: PRT
<213> ORGANISM: Artificial Sequence
<220> FEATURE:
<223> OTHER INFORMATION: AMINO ACID OF FLS:L482S

<400> SEQUENCE: 10

Met Ala Met Ile Thr Gly Gly Glu Leu Val Val Arg Thr Leu Ile Lys
1               5                   10                  15

Ala Gly Val Glu His Leu Phe Gly Leu His Gly Ile His Ile Asp Thr
            20                  25                  30

Ile Phe Gln Ala Cys Leu Asp His Asp Val Pro Ile Ile Asp Thr Arg
        35                  40                  45

His Glu Ala Ala Ala Gly His Ala Ala Glu Gly Tyr Ala Arg Ala Gly
    50                  55                  60

Ala Lys Leu Gly Val Ala Leu Val Thr Ala Gly Gly Gly Phe Thr Asn
65                  70                  75                  80

Ala Val Thr Pro Ile Ala Asn Ala Arg Thr Asp Arg Thr Pro Val Leu
                85                  90                  95

Phe Leu Thr Gly Ser Gly Ala Leu Arg Asp Asp Glu Thr Asn Thr Leu
            100                 105                 110

Gln Ala Gly Ile Asp Gln Val Ala Met Ala Ala Pro Ile Thr Lys Trp
        115                 120                 125

Ala His Arg Val Met Ala Thr Glu His Ile Pro Arg Leu Val Met Gln
    130                 135                 140

Ala Ile Arg Ala Ala Leu Ser Ala Pro Arg Gly Pro Val Leu Leu Asp
145                 150                 155                 160

Leu Pro Trp Asp Ile Leu Met Asn Gln Ile Asp Glu Asp Ser Val Ile
                165                 170                 175

Ile Pro Asp Leu Val Leu Ser Ala His Gly Ala His Pro Asp Pro Ala
            180                 185                 190

Asp Leu Asp Gln Ala Leu Ala Leu Leu Arg Lys Ala Glu Arg Pro Val
        195                 200                 205

Ile Val Leu Gly Ser Glu Ala Ser Arg Thr Ala Arg Lys Thr Ala Leu
    210                 215                 220

Ser Ala Phe Val Ala Ala Thr Gly Val Pro Val Phe Ala Asp Tyr Glu
225                 230                 235                 240

Gly Leu Ser Met Leu Ser Gly Leu Pro Asp Ala Met Arg Gly Gly Leu
                245                 250                 255
```

```
Val Gln Asn Leu Tyr Ser Phe Ala Lys Ala Asp Ala Ala Pro Asp Leu
            260                 265                 270

Val Leu Met Leu Gly Ala Arg Phe Gly Leu Asn Thr Gly His Gly Ser
        275                 280                 285

Gly Gln Leu Ile Pro His Ser Ala Gln Val Ile Gln Val Asp Pro Asp
    290                 295                 300

Ala Cys Glu Leu Gly Arg Leu Gln Gly Ile Ala Leu Gly Ile Val Ala
305                 310                 315                 320

Asp Val Gly Gly Thr Ile Glu Ala Leu Ala Gln Ala Thr Ala Gln Asp
                325                 330                 335

Ala Ala Trp Pro Asp Arg Gly Asp Trp Cys Ala Lys Val Thr Asp Leu
            340                 345                 350

Ala Gln Glu Arg Tyr Ala Ser Ile Ala Ala Lys Ser Ser Glu His
        355                 360                 365

Ala Leu His Pro Phe His Ala Ser Gln Val Ile Ala Lys His Val Asp
    370                 375                 380

Ala Gly Val Thr Val Ala Asp Gly Gly Leu Thr Tyr Leu Trp Leu
385                 390                 395                 400

Ser Glu Val Met Ser Arg Val Lys Pro Gly Gly Phe Leu Cys His Gly
                405                 410                 415

Tyr Leu Asn Ser Met Gly Val Gly Phe Gly Thr Ala Leu Gly Ala Gln
            420                 425                 430

Val Ala Asp Leu Glu Ala Gly Arg Arg Thr Ile Leu Val Thr Gly Asp
        435                 440                 445

Gly Ser Val Gly Tyr Ser Ile Gly Glu Phe Asp Thr Leu Val Arg Lys
    450                 455                 460

Gln Leu Pro Leu Ile Val Ile Met Asn Asn Gln Ser Trp Gly Trp
465                 470                 475                 480

Thr Ser His Phe Gln Gln Leu Ala Val Gly Pro Asn Arg Val Thr Gly
                485                 490                 495

Thr Arg Leu Glu Asn Gly Ser Tyr His Gly Val Ala Ala Phe Gly
            500                 505                 510

Ala Asp Gly Tyr His Val Asp Ser Val Glu Ser Phe Ser Ala Ala Leu
    515                 520                 525

Ala Gln Ala Leu Ala His Asn Arg Pro Ala Cys Ile Asn Val Ala Val
530                 535                 540

Ala Leu Asp Pro Ile Pro Pro Glu Glu Leu Ile Leu Ile Gly Met Asp
545                 550                 555                 560

Pro Phe Ala

<210> SEQ ID NO 11
<211> LENGTH: 563
<212> TYPE: PRT
<213> ORGANISM: Artificial Sequence
<220> FEATURE:
<223> OTHER INFORMATION: AMINO ACID OF FLS:L482R

<400> SEQUENCE: 11

Met Ala Met Ile Thr Gly Gly Glu Leu Val Val Arg Thr Leu Ile Lys
1               5                   10                  15

Ala Gly Val Glu His Leu Phe Gly Leu His Gly Ile His Ile Asp Thr
            20                  25                  30

Ile Phe Gln Ala Cys Leu Asp His Asp Val Pro Ile Ile Asp Thr Arg
        35                  40                  45
```

-continued

His Glu Ala Ala Ala Gly His Ala Ala Glu Gly Tyr Ala Arg Ala Gly
    50                  55                  60

Ala Lys Leu Gly Val Ala Leu Val Thr Ala Gly Gly Phe Thr Asn
65                  70                  75                  80

Ala Val Thr Pro Ile Ala Asn Ala Arg Thr Asp Arg Thr Pro Val Leu
                85                  90                  95

Phe Leu Thr Gly Ser Gly Ala Leu Arg Asp Asp Glu Thr Asn Thr Leu
                100                 105                 110

Gln Ala Gly Ile Asp Gln Val Ala Met Ala Ala Pro Ile Thr Lys Trp
            115                 120                 125

Ala His Arg Val Met Ala Thr Glu His Ile Pro Arg Leu Val Met Gln
130                 135                 140

Ala Ile Arg Ala Ala Leu Ser Ala Pro Arg Gly Pro Val Leu Leu Asp
145                 150                 155                 160

Leu Pro Trp Asp Ile Leu Met Asn Gln Ile Asp Glu Asp Ser Val Ile
                165                 170                 175

Ile Pro Asp Leu Val Leu Ser Ala His Gly Ala His Pro Asp Pro Ala
            180                 185                 190

Asp Leu Asp Gln Ala Leu Ala Leu Leu Arg Lys Ala Glu Arg Pro Val
        195                 200                 205

Ile Val Leu Gly Ser Glu Ala Ser Arg Thr Ala Arg Lys Thr Ala Leu
    210                 215                 220

Ser Ala Phe Val Ala Ala Thr Gly Val Pro Val Phe Ala Asp Tyr Glu
225                 230                 235                 240

Gly Leu Ser Met Leu Ser Gly Leu Pro Asp Ala Met Arg Gly Gly Leu
                245                 250                 255

Val Gln Asn Leu Tyr Ser Phe Ala Lys Ala Asp Ala Ala Pro Asp Leu
            260                 265                 270

Val Leu Met Leu Gly Ala Arg Phe Gly Leu Asn Thr Gly His Gly Ser
        275                 280                 285

Gly Gln Leu Ile Pro His Ser Ala Gln Val Ile Gln Val Asp Pro Asp
    290                 295                 300

Ala Cys Glu Leu Gly Arg Leu Gln Gly Ile Ala Leu Gly Ile Val Ala
305                 310                 315                 320

Asp Val Gly Gly Thr Ile Glu Ala Leu Ala Gln Ala Thr Ala Gln Asp
                325                 330                 335

Ala Ala Trp Pro Asp Arg Gly Asp Trp Cys Ala Lys Val Thr Asp Leu
            340                 345                 350

Ala Gln Glu Arg Tyr Ala Ser Ile Ala Ala Lys Ser Ser Glu His
        355                 360                 365

Ala Leu His Pro Phe His Ala Ser Gln Val Ile Ala Lys His Val Asp
    370                 375                 380

Ala Gly Val Thr Val Ala Asp Gly Gly Leu Thr Tyr Leu Trp Leu
385                 390                 395                 400

Ser Glu Val Met Ser Arg Val Lys Pro Gly Gly Phe Leu Cys His Gly
                405                 410                 415

Tyr Leu Asn Ser Met Gly Val Gly Phe Gly Thr Ala Leu Gly Ala Gln
            420                 425                 430

Val Ala Asp Leu Glu Ala Gly Arg Arg Thr Ile Leu Val Thr Gly Asp
        435                 440                 445

Gly Ser Val Gly Tyr Ser Ile Gly Glu Phe Asp Thr Leu Val Arg Lys
    450                 455                 460

Gln Leu Pro Leu Ile Val Ile Ile Met Asn Asn Gln Ser Trp Gly Trp

```
                        465                 470                 475                 480
Thr Arg His Phe Gln Gln Leu Ala Val Gly Pro Asn Arg Val Thr Gly
                485                 490                 495

Thr Arg Leu Glu Asn Gly Ser Tyr His Gly Val Ala Ala Phe Gly
            500                 505                 510

Ala Asp Gly Tyr His Val Asp Ser Val Glu Ser Phe Ser Ala Ala Leu
            515                 520                 525

Ala Gln Ala Leu Ala His Asn Arg Pro Ala Cys Ile Asn Val Ala Val
        530                 535                 540

Ala Leu Asp Pro Ile Pro Pro Glu Glu Leu Ile Leu Ile Gly Met Asp
545                 550                 555                 560

Pro Phe Ala

<210> SEQ ID NO 12
<211> LENGTH: 563
<212> TYPE: PRT
<213> ORGANISM: Artificial Sequence
<220> FEATURE:
<223> OTHER INFORMATION: AMINO ACID OF FLS:L482E

<400> SEQUENCE: 12

Met Ala Met Ile Thr Gly Gly Glu Leu Val Val Arg Thr Leu Ile Lys
1               5                   10                  15

Ala Gly Val Glu His Leu Phe Gly Leu His Gly Ile His Ile Asp Thr
            20                  25                  30

Ile Phe Gln Ala Cys Leu Asp His Asp Val Pro Ile Ile Asp Thr Arg
        35                  40                  45

His Glu Ala Ala Ala Gly His Ala Ala Glu Gly Tyr Ala Arg Ala Gly
    50                  55                  60

Ala Lys Leu Gly Val Ala Leu Val Thr Ala Gly Gly Phe Thr Asn
65                  70                  75                  80

Ala Val Thr Pro Ile Ala Asn Ala Arg Thr Asp Arg Thr Pro Val Leu
                85                  90                  95

Phe Leu Thr Gly Ser Gly Ala Leu Arg Asp Asp Glu Thr Asn Thr Leu
            100                 105                 110

Gln Ala Gly Ile Asp Gln Val Ala Met Ala Ala Pro Ile Thr Lys Trp
        115                 120                 125

Ala His Arg Val Met Ala Thr Glu His Ile Pro Arg Leu Val Met Gln
    130                 135                 140

Ala Ile Arg Ala Ala Leu Ser Ala Pro Arg Gly Pro Val Leu Leu Asp
145                 150                 155                 160

Leu Pro Trp Asp Ile Leu Met Asn Gln Ile Asp Glu Asp Ser Val Ile
                165                 170                 175

Ile Pro Asp Leu Val Leu Ser Ala His Gly Ala His Pro Asp Pro Ala
            180                 185                 190

Asp Leu Asp Gln Ala Leu Ala Leu Leu Arg Lys Ala Glu Arg Pro Val
        195                 200                 205

Ile Val Leu Gly Ser Glu Ala Ser Arg Thr Ala Arg Lys Thr Ala Leu
    210                 215                 220

Ser Ala Phe Val Ala Ala Thr Gly Val Pro Val Phe Ala Asp Tyr Glu
225                 230                 235                 240

Gly Leu Ser Met Leu Ser Gly Leu Pro Asp Ala Met Arg Gly Gly Leu
                245                 250                 255

Val Gln Asn Leu Tyr Ser Phe Ala Lys Ala Asp Ala Ala Pro Asp Leu
            260                 265                 270
```

Val Leu Met Leu Gly Ala Arg Phe Gly Leu Asn Thr Gly His Gly Ser
            275                 280                 285

Gly Gln Leu Ile Pro His Ser Ala Gln Val Ile Gln Val Asp Pro Asp
        290                 295                 300

Ala Cys Glu Leu Gly Arg Leu Gln Gly Ile Ala Leu Gly Ile Val Ala
305                 310                 315                 320

Asp Val Gly Gly Thr Ile Glu Ala Leu Ala Gln Ala Thr Ala Gln Asp
                325                 330                 335

Ala Ala Trp Pro Asp Arg Gly Asp Trp Cys Ala Lys Val Thr Asp Leu
            340                 345                 350

Ala Gln Glu Arg Tyr Ala Ser Ile Ala Ala Lys Ser Ser Glu His
        355                 360                 365

Ala Leu His Pro Phe His Ala Ser Gln Val Ile Ala Lys His Val Asp
    370                 375                 380

Ala Gly Val Thr Val Ala Asp Gly Gly Leu Thr Tyr Leu Trp Leu
385                 390                 395                 400

Ser Glu Val Met Ser Arg Val Lys Pro Gly Gly Phe Leu Cys His Gly
                405                 410                 415

Tyr Leu Asn Ser Met Gly Val Gly Phe Gly Thr Ala Leu Gly Ala Gln
            420                 425                 430

Val Ala Asp Leu Glu Ala Gly Arg Arg Thr Ile Leu Val Thr Gly Asp
        435                 440                 445

Gly Ser Val Gly Tyr Ser Ile Gly Glu Phe Asp Thr Leu Val Arg Lys
    450                 455                 460

Gln Leu Pro Leu Ile Val Ile Ile Met Asn Asn Gln Ser Trp Gly Trp
465                 470                 475                 480

Thr Glu His Phe Gln Gln Leu Ala Val Gly Pro Asn Arg Val Thr Gly
                485                 490                 495

Thr Arg Leu Glu Asn Gly Ser Tyr His Gly Val Ala Ala Ala Phe Gly
            500                 505                 510

Ala Asp Gly Tyr His Val Asp Ser Val Glu Ser Phe Ser Ala Ala Leu
        515                 520                 525

Ala Gln Ala Leu Ala His Asn Arg Pro Ala Cys Ile Asn Val Ala Val
    530                 535                 540

Ala Leu Asp Pro Ile Pro Pro Glu Glu Leu Ile Leu Ile Gly Met Asp
545                 550                 555                 560

Pro Phe Ala

<210> SEQ ID NO 13
<211> LENGTH: 1056
<212> TYPE: DNA
<213> ORGANISM: Artificial Sequence
<220> FEATURE:
<223> OTHER INFORMATION: Full-length BDH

<400> SEQUENCE: 13
atgaaaggtt tgcaatgtt aggtattaac aaattaggat ggattgaaaa gaaaaaccca      60
gtgccaggtc cttatgatgc gattgtacat cctctagctg tatccccatg tacatcagat     120
atacatacgg tttttgaagg agcacttggt aataggaaa atatgatttt aggccatgaa     180
gctgtaggtg aaatagccga agttggcagc gaagttaaag attttaaagt tggcgataga     240
gttatcgtac catgcacaac acctgactgg agatctttag aagtccaagc tggttttcag     300
cagcattcaa acggtatgct tgcaggatgg aagttttcca attttaaaga tggtgtattt     360

```
gcagattact ttcatgtaaa cgatgcagat atgaatcttg ccatactccc agatgaaata    420
cctttagaaa gtgcagttat gatgacagac atgatgacta ctggttttca tggagcagaa    480
cttgcagaca taaaaatggg ctccagcgtt gtagtaattg gtataggagc tgttggatta    540
atgggaatag ccggttccaa acttcgagga gcaggcagaa ttatcggtgt tggaagcaga    600
cctgtttgtg ttgaaacagc taaattttat ggagcaactg atattgtaaa ttataaaaat    660
ggtgatatag ttgaacaaat catggactta actcatggta aaggtgtaga ccgtgtaatc    720
atggcaggcg gtggtgctga aacactagca caagcagtaa ctatggttaa acctggcggc    780
gtaatttcta acatcaacta ccatggaagc ggtgatactt taccaatacc tcgtgttcaa    840
tggggctgcg gcatggctca aaaactata agaggaggat tatgccccgg cggacgtctt    900
agaatggaaa tgctaagaga tcttgttcta tataaacgtg ttgatttgag taaacttgtt    960
actcatgtat ttgatggtgc agaaaatatt gaaaaggccc ttttgcttat gaaaaataag   1020
ccaaaagatt taattaaatc agtagttaca ttctaa                              1056
```

<210> SEQ ID NO 14
<211> LENGTH: 351
<212> TYPE: PRT
<213> ORGANISM: Artificial Sequence
<220> FEATURE:
<223> OTHER INFORMATION: AMINO ACID OF BDH

<400> SEQUENCE: 14

```
Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Gly Ser Arg Pro Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
225                 230                 235                 240
```

```
Met Ala Gly Gly Gly Ala Glu Thr Leu Ala Gln Val Thr Met Val
                245                 250                 255

Lys Pro Gly Gly Val Ile Ser Asn Ile Asn Tyr His Gly Ser Gly Asp
        260                 265                 270

Thr Leu Pro Ile Pro Arg Val Gln Trp Gly Cys Gly Met Ala His Lys
            275                 280                 285

Thr Ile Arg Gly Gly Leu Cys Pro Gly Gly Arg Leu Arg Met Glu Met
        290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
            325                 330                 335

Met Lys Asn Lys Pro Lys Asp Leu Ile Lys Ser Val Val Thr Phe
            340                 345                 350

<210> SEQ ID NO 15
<211> LENGTH: 1056
<212> TYPE: DNA
<213> ORGANISM: Artificial Sequence
<220> FEATURE:
<223> OTHER INFORMATION: BDH:S199A

<400> SEQUENCE: 15
atgaaaggtt ttgcaatgtt aggtattaac aaattaggat ggattgaaaa gaaaaaccca     60
gtgccaggtc cttatgatgc gattgtacat cctctagctg tatccccatg tacatcagat    120
atacatacgg tttttgaagg agcacttggt aatagggaaa atatgatttt aggccatgaa    180
gctgtaggtg aaatagccga agttggcagc gaagttaaag atttaaagt tggcgataga    240 gttatcgtac catgcacaac acctgactgg agatctttag aagtccaagc tggttttcag    300
cagcattcaa acggtatgct tgcaggatgg aagttttcca attttaaaga tggtgtattt    360
gcagattact ttcatgtaaa cgatgcagat atgaatcttg ccatactccc agatgaaata    420
cctttagaaa gtgcagttat gatgacagac atgatgacta ctggttttca tggagcagaa    480
cttgcagaca taaaaatggg ctccagcgtt gtagtaattg gtagaggagc tgttggatta    540
atgggaatag ccggttccaa acttcgagga gcaggcagaa ttatcggtgt ggagccaga    600 cctgtttgtg ttgaaacagc taaatttat ggagcaactg atattgtaaa ttataaaaat    660
ggtgatatag ttgaacaaat catggactta actcatggta aggtgtaga ccgtgtaatc    720 atggcaggcg gtggtgctga acactagca caagcagtaa ctatggttaa acctggcggc    780
gtaatttcta acatcaacta ccatggaagc ggtgatactt taccaatacc tcgtgttcaa    840
tggggctgcg gcatggctca caaaactata agaggaggat atgccccgg cggacgtctt    900 agaatggaaa tgctaagaga tcttgttcta tataaacgtg ttgatttgag taaacttgtt    960
actcatgtat ttgatggtgc agaaaatatt gaaaaggccc ttttgcttat gaaaaataag   1020
ccaaaagatt taattaaatc agtagttaca ttctaa                             1056

<210> SEQ ID NO 16
<211> LENGTH: 351
<212> TYPE: PRT
<213> ORGANISM: Artificial Sequence
<220> FEATURE:
<223> OTHER INFORMATION: AMINO ACID OF BDH:S199A

<400> SEQUENCE: 16

Met Lys Gly Phe Ala Met Leu Gly Ile Asn Lys Leu Gly Trp Ile Glu
1               5                   10                  15
```

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Gly Ala Arg Pro Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
    290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350

<210> SEQ ID NO 17
<211> LENGTH: 2957
<212> TYPE: DNA
<213> ORGANISM: Artificial Sequence
<220> FEATURE:
<223> OTHER INFORMATION: Full-length DDH

<400> SEQUENCE: 17
atgaaacgtc aaaaacgatt tgaagaatta gagaaacgcc cgatccattt agacggtttc      60
gttaaggaat ggcctgaaga aggcttcgtt gccatgatgg ggcctaatga cccaaagcca     120
agcatcaaga ttgaaaacgg caaggttact gaaatggata gtaaaccagc tgctgacttc     180

```
gatctgattg atctctacat cgcaaaatat ggcattaagc ttgaaaatgc tgagaaagta      240
atggcgatgg attccactaa gatcgccaat atgctctgtg accccaatgt gccacgtaaa      300
gacatcattg agattacaac ggcgatgacg ccggccaaag ctgaagaagt tatcagcaaa      360
ttgaactttg ccgaaatgat tatggcaacg caaaaaatgc ggccacggcg acaccagca       420 acgcaatgtc acgttaccaa tattcgggat aatcccgttc aaattgctgc tgacgctgcc      480
gatgctgcct tacggggttt cccggaacaa gaaaccacga cggccgttgc ccggtatgcc      540
ccattgaatg ccatctcgtt gatggtgggg cgcaaaccg gtcgtcctgg tgttatcacc       600
caatgctcgg ttgaagaagc agaagaattg agtttaggga tgcggggctt cactggctac      660
gccgaaacca tttctgttta cggtaccgat aaggtcttca ctgatggtga tgatacacca      720
tggtccaaag gcttcttagc ttcctgctat gcttcgcggg ggttgaagat gcggtttacg      780
tctggttctg gttccgaagt tatgatgggt tataccgaag gtaagtccat gttataccctc     840 gaatcacgtt gtatcttcat taccaaagcg tccggtgttc aaggcctcca aaacggtggg      900
gttagttgta ttgggattcc agggtctgtt ccttctggga ttcgctccgt cttgggtgaa      960
aacctattgt gcatgatgct tgaccttgaa tgtgcgtctg ctaatgacca agcgttctcc     1020
cattctgata tgcggcggac agaacggtta ttaggccaat tcattgccgg aaccgattac     1080
atttcttctg ttactcctc aacacctaac tatgacaaca cgtttgcggg gtcaaacacc      1140
gatggcttgg actacgatga ttactacgtt atggaacgcg acttggccat caacggtggg     1200
attcacccag ttgatgaaca acaatcatc aaagcccgca acaaggctgc acgggccctt      1260
caaggtgtct ttgaagatct aggttttgcct aagattaccg atgaagaagt ggaagcggca    1320
acttacgcca acacctctaa ggatatgcca gaacggaaca tggttgaaga tatgaaggcc     1380
gcccaagatc tgatggatcg cggcattacc ggggtcgata ttgttaaagc cttgttcaac     1440
cacggattta aggatgttgc ccaagccgtt ttagatttgc aaaagcaaaa ggtttgtggg     1500
gacttcttac agacatccgc tattttcgac agcaagtggc atgtcatttc cgccgtcaac     1560
gatgccaatg actatcaagg tcctggtacg ggttaccggt tggaagaaga tacggaagaa     1620
tgggaacgca tcaagaactt accgtttgcc attgatccac aaaacatgca gctttagtcg     1680 aaaaggggt  taacactatg ctcaagaaa  ttgatgaaaa cttattgcgg aatattatcc     1740
gtgatgtgat tgcggaaacc caaacggggg acacgccaat ctcatttaaa gctgatgcac     1800
cagcagcgtc atcagctacg acggcaacgg ctgcaccagt taatggtgac ggcccagaac     1860
cggaaaaacc agttgactgg ttcaaacacg ttggggttgc caagcccggc tattcacgtg     1920
atgaagtcgt gattgctgtg gcaccagcct ttgcagaagt gatggaccat aacttgaccg     1980
gaatcagtca taaagaaatt ttacgacaga tggttgctgg tattgaagaa gaaggactga     2040
aggcccgaat tgtgaaagtc taccggactt ctgacgtttc cttctgtggt gccgaagggg     2100
atcatttatc aggttctggc atcgccattg ccattcaatc caaggggacg acgatcattc     2160
accaaaagga ccaagaacca ttgtccaact tggaattatt cccacaagca cctgtcttgg     2220
atggtgatac ctaccgggct atcggcaaga atgcagccga atacgctaaa ggaatgtcac     2280
caagccccgt tccaacggtt aatgaccaaa tggctcgggt tcaataccag gccttgtctg     2340
ccttgatgca tatcaaggaa acgaagcagg tcgttatggg gaaacccgct gaacaaatcg     2400
aagtcaactt taactaggag gaatgggtca tgagtgaaat tgatgactta gtagcaaaaa     2460
tcgtccaaca aattggtggc actgaggccg ctgatcagac gactgccacg cctacgtcaa     2520
```

```
cggcgacgca gacgcagcat gcagcattat cgaaacaaga ttatccactg tactctaagc    2580
acccagagct cgtacattca ccgtctggga aagctttgaa cgatatcact ttggataatg    2640
ttctcaacga tgatattaag gccaatgatt tacgaattac gccggatacc ttacggatgc    2700
aaggtgaagt ggccaacgat gctggtcggg atgcggttca acgtaacttc agcgggcgt    2760 cagaattgac ctctattccg gatgatcggt tactggaaat gtacaacgcc ttacgaccat    2820
accggtctac taaagcggaa ttattagcga tttcagccga gttaaaggat aaatatcatg    2880
ccccagtgaa cgccggatgg tttgcggaag cggccgacta ctacgaatcc cgtaagaagc    2940
tgaagggtga taactag                                                  2957
```

<210> SEQ ID NO 18
<211> LENGTH: 974
<212> TYPE: PRT
<213> ORGANISM: Artificial Sequence
<220> FEATURE:
<223> OTHER INFORMATION: AMINO ACID OF DDH
<220> FEATURE:
<221> NAME/KEY: MISC_FEATURE
<222> LOCATION: (1)..(974)
<223> OTHER INFORMATION: all Xaa is independently any amino acid

<400> SEQUENCE: 18

```
Met Lys Arg Gln Lys Arg Phe Glu Glu Leu Glu Lys Arg Pro Ile His
1               5                   10                  15

Leu Asp Gly Phe Val Lys Glu Trp Pro Glu Gly Phe Val Ala Met
            20                  25                  30

Met Gly Pro Asn Asp Pro Lys Pro Ser Ile Lys Ile Glu Asn Gly Lys
        35                  40                  45

Val Thr Glu Met Asp Ser Lys Pro Ala Ala Asp Phe Asp Leu Ile Asp
    50                  55                  60

Leu Tyr Ile Ala Lys Tyr Gly Ile Lys Leu Glu Asn Ala Glu Lys Val
65                  70                  75                  80

Met Ala Met Asp Ser Thr Lys Ile Ala Asn Met Leu Cys Asp Pro Asn
                85                  90                  95

Val Pro Arg Lys Asp Ile Ile Glu Ile Thr Thr Ala Met Thr Pro Ala
            100                 105                 110

Lys Ala Glu Glu Val Ile Ser Lys Leu Asn Phe Ala Glu Met Ile Met
        115                 120                 125

Ala Thr Gln Lys Met Arg Pro Arg Thr Pro Ala Thr Gln Cys His
    130                 135                 140

Val Thr Asn Ile Arg Asp Asn Pro Val Gln Ile Ala Ala Asp Ala Ala
145                 150                 155                 160

Asp Ala Ala Leu Arg Gly Phe Pro Glu Gln Glu Thr Thr Thr Ala Val
                165                 170                 175

Ala Arg Tyr Ala Pro Leu Asn Ala Ile Ser Leu Met Val Gly Ala Gln
            180                 185                 190

Thr Gly Arg Pro Gly Val Ile Thr Gln Cys Ser Val Glu Glu Ala Glu
        195                 200                 205

Glu Leu Ser Leu Gly Met Arg Gly Phe Thr Gly Tyr Ala Glu Thr Ile
    210                 215                 220

Ser Val Tyr Gly Thr Asp Lys Val Phe Thr Asp Gly Asp Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ser Gly Ser Glu Val Met Met Gly Tyr Thr
```

```
              260                 265                 270
Glu Gly Lys Ser Met Leu Tyr Leu Glu Ser Arg Cys Ile Phe Ile Thr
            275                 280                 285

Lys Ala Ser Gly Val Gln Gly Leu Gln Asn Gly Gly Val Ser Cys Ile
        290                 295                 300

Gly Ile Pro Gly Ser Val Pro Ser Gly Ile Arg Ser Val Leu Gly Glu
305                 310                 315                 320

Asn Leu Leu Cys Met Met Leu Asp Leu Glu Cys Ala Ser Ala Asn Asp
                325                 330                 335

Gln Ala Phe Ser His Ser Asp Met Arg Arg Thr Glu Arg Leu Leu Gly
            340                 345                 350

Gln Phe Ile Ala Gly Thr Asp Tyr Ile Ser Ser Gly Tyr Ser Ser Thr
        355                 360                 365

Pro Asn Tyr Asp Asn Thr Phe Ala Gly Ser Asn Thr Asp Gly Leu Asp
    370                 375                 380

Tyr Asp Asp Tyr Tyr Val Met Glu Arg Asp Leu Ala Ile Asn Gly Gly
385                 390                 395                 400

Ile His Pro Val Asp Glu Gln Thr Ile Ile Lys Ala Arg Asn Lys Ala
                405                 410                 415

Ala Arg Ala Leu Gln Gly Val Phe Glu Asp Leu Gly Leu Pro Lys Ile
            420                 425                 430

Thr Asp Glu Glu Val Glu Ala Ala Thr Tyr Ala Asn Thr Ser Lys Asp
        435                 440                 445

Met Pro Glu Arg Asn Met Val Glu Asp Met Lys Ala Ala Gln Asp Leu
    450                 455                 460

Met Asp Arg Gly Ile Thr Gly Val Asp Ile Val Lys Ala Leu Phe Asn
465                 470                 475                 480

His Gly Phe Lys Asp Val Ala Gln Ala Val Leu Asp Leu Gln Lys Gln
                485                 490                 495

Lys Val Cys Gly Asp Phe Leu Gln Thr Ser Ala Ile Phe Asp Ser Lys
            500                 505                 510

Trp His Val Ile Ser Ala Val Asn Asp Ala Asn Asp Tyr Gln Gly Pro
        515                 520                 525

Gly Thr Gly Tyr Arg Leu Glu Glu Asp Thr Glu Glu Trp Glu Arg Ile
    530                 535                 540

Lys Asn Leu Pro Phe Ala Ile Asp Pro Gln Asn Met Gln Leu Xaa Met
545                 550                 555                 560

Ala Gln Glu Ile Asp Glu Asn Leu Leu Arg Asn Ile Ile Arg Asp Val
                565                 570                 575

Ile Ala Glu Thr Gln Thr Gly Asp Thr Pro Ile Ser Phe Lys Ala Asp
            580                 585                 590

Ala Pro Ala Ser Ser Ala Thr Thr Ala Thr Ala Pro Val Asn
        595                 600                 605              Asn

Gly Asp Gly Pro Glu Pro Glu Lys Pro Val Asp Trp Phe Lys His Val
    610                 615                 620

Gly Val Ala Lys Pro Gly Tyr Ser Arg Asp Glu Val Ile Ala Val
625                 630                 635                 640

Ala Pro Ala Phe Ala Glu Val Met Asp His Asn Leu Thr Gly Ile Ser
                645                 650                 655

His Lys Glu Ile Leu Arg Gln Met Val Ala Gly Ile Glu Glu Glu Gly
            660                 665                 670

Leu Lys Ala Arg Ile Val Lys Val Tyr Arg Thr Ser Asp Val Ser Phe
        675                 680                 685
```

```
Cys Gly Ala Glu Gly Asp His Leu Ser Gly Ser Gly Ile Ala Ile Ala
            690                 695                 700

Ile Gln Ser Lys Gly Thr Thr Ile Ile His Gln Lys Asp Gln Glu Pro
705                 710                 715                 720

Leu Ser Asn Leu Glu Leu Phe Pro Gln Ala Pro Val Leu Asp Gly Asp
                725                 730                 735

Thr Tyr Arg Ala Ile Gly Lys Asn Ala Ala Glu Tyr Ala Lys Gly Met
            740                 745                 750

Ser Pro Ser Pro Val Pro Thr Val Asn Asp Gln Met Ala Arg Val Gln
        755                 760                 765

Tyr Gln Ala Leu Ser Ala Leu Met His Ile Lys Glu Thr Lys Gln Val
770                 775                 780

Val Met Gly Lys Pro Ala Glu Gln Ile Glu Val Asn Phe Asn Xaa Met
785                 790                 795                 800

Ser Glu Ile Asp Asp Leu Val Ala Lys Ile Val Gln Ile Gly Gly
                805                 810                 815

Thr Glu Ala Ala Asp Gln Thr Thr Ala Thr Pro Thr Ser Thr Ala Thr
                820                 825                 830

Gln Thr Gln His Ala Ala Leu Ser Lys Gln Asp Tyr Pro Leu Tyr Ser
            835                 840                 845

Lys His Pro Glu Leu Val His Ser Pro Ser Gly Lys Ala Leu Asn Asp
850                 855                 860

Ile Thr Leu Asp Asn Val Leu Asn Asp Ile Lys Ala Asn Asp Leu
865                 870                 875                 880

Arg Ile Thr Pro Asp Thr Leu Arg Met Gln Gly Glu Val Ala Asn Asp
                885                 890                 895

Ala Gly Arg Asp Ala Val Gln Arg Asn Phe Gln Arg Ala Ser Glu Leu
            900                 905                 910

Thr Ser Ile Pro Asp Asp Arg Leu Leu Glu Met Tyr Asn Ala Leu Arg
        915                 920                 925

Pro Tyr Arg Ser Thr Lys Ala Glu Leu Leu Ala Ile Ser Ala Glu Leu
930                 935                 940

Lys Asp Lys Tyr His Ala Pro Val Asn Ala Gly Trp Phe Ala Glu Ala
945                 950                 955                 960

Ala Asp Tyr Tyr Glu Ser Arg Lys Lys Leu Lys Gly Asp Asn
                965                 970

<210> SEQ ID NO 19
<211> LENGTH: 974
<212> TYPE: PRT
<213> ORGANISM: Artificial Sequence
<220> FEATURE:
<223> OTHER INFORMATION: AMINO ACID OF DDH: S302A
<220> FEATURE:
<221> NAME/KEY: MISC_FEATURE
<222> LOCATION: (1)..(974)
<223> OTHER INFORMATION: all Xaa is independently any amino acid

<400> SEQUENCE: 19

Met Lys Arg Gln Lys Arg Phe Glu Glu Leu Glu Lys Arg Pro Ile His
1               5                   10                  15

Leu Asp Gly Phe Val Lys Glu Trp Pro Glu Glu Gly Phe Val Ala Met
                20                  25                  30

Met Gly Pro Asn Asp Pro Lys Pro Ser Ile Lys Ile Glu Asn Gly Lys
            35                  40                  45

Val Thr Glu Met Asp Ser Lys Pro Ala Ala Asp Phe Asp Leu Ile Asp
```

```
            50                  55                  60
Leu Tyr Ile Ala Lys Tyr Gly Ile Lys Leu Glu Asn Ala Glu Lys Val
 65                  70                  75                  80

Met Ala Met Asp Ser Thr Lys Ile Ala Asn Met Leu Cys Asp Pro Asn
                     85                  90                  95

Val Pro Arg Lys Asp Ile Ile Glu Ile Thr Thr Ala Met Thr Pro Ala
                100                 105                 110

Lys Ala Glu Glu Val Ile Ser Lys Leu Asn Phe Ala Glu Met Ile Met
                115                 120                 125

Ala Thr Gln Lys Met Arg Pro Arg Thr Pro Ala Thr Gln Cys His
    130                 135                 140

Val Thr Asn Ile Arg Asp Asn Pro Val Gln Ile Ala Ala Asp Ala Ala
145                 150                 155                 160

Asp Ala Ala Leu Arg Gly Phe Pro Glu Gln Glu Thr Thr Thr Ala Val
                165                 170                 175

Ala Arg Tyr Ala Pro Leu Asn Ala Ile Ser Leu Met Val Gly Ala Gln
                180                 185                 190

Thr Gly Arg Pro Gly Val Ile Thr Gln Cys Ser Val Glu Glu Ala Glu
            195                 200                 205

Glu Leu Ser Leu Gly Met Arg Gly Phe Thr Gly Tyr Ala Glu Thr Ile
    210                 215                 220

Ser Val Tyr Gly Thr Asp Lys Val Phe Thr Asp Gly Asp Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ser Gly Glu Val Met Met Gly Tyr Thr
                260                 265                 270

Glu Gly Lys Ser Met Leu Tyr Leu Glu Ser Arg Cys Ile Phe Ile Thr
            275                 280                 285

Lys Ala Ser Gly Val Gln Gly Leu Gln Asn Gly Gly Val Ala Cys Ile
            290                 295                 300

Gly Ile Pro Gly Ser Val Pro Ser Gly Ile Arg Ser Val Leu Gly Glu
305                 310                 315                 320

Asn Leu Leu Cys Met Met Leu Asp Leu Glu Cys Ala Ser Ala Asn Asp
                325                 330                 335

Gln Ala Phe Ser His Ser Asp Met Arg Arg Thr Glu Arg Leu Leu Gly
                340                 345                 350

Gln Phe Ile Ala Gly Thr Asp Tyr Ile Ser Ser Gly Tyr Ser Ser Thr
            355                 360                 365

Pro Asn Tyr Asp Asn Thr Phe Ala Gly Ser Asn Thr Asp Gly Leu Asp
            370                 375                 380

Tyr Asp Asp Tyr Tyr Val Met Glu Arg Asp Leu Ala Ile Asn Gly Gly
385                 390                 395                 400

Ile His Pro Val Asp Glu Gln Thr Ile Ile Lys Ala Arg Asn Lys Ala
                405                 410                 415

Ala Arg Ala Leu Gln Gly Val Phe Glu Asp Leu Gly Leu Pro Lys Ile
                420                 425                 430

Thr Asp Glu Glu Val Glu Ala Ala Thr Tyr Ala Asn Thr Ser Lys Asp
            435                 440                 445

Met Pro Glu Arg Asn Met Val Glu Asp Met Lys Ala Ala Gln Asp Leu
            450                 455                 460

Met Asp Arg Gly Ile Thr Gly Val Asp Ile Val Lys Ala Leu Phe Asn
465                 470                 475                 480
```

```
His Gly Phe Lys Asp Val Ala Gln Ala Val Leu Asp Leu Gln Lys Gln
            485                 490                 495

Lys Val Cys Gly Asp Phe Leu Gln Thr Ser Ala Ile Phe Asp Ser Lys
            500                 505                 510

Trp His Val Ile Ser Ala Val Asn Asp Ala Asn Asp Tyr Gln Gly Pro
            515                 520                 525

Gly Thr Gly Tyr Arg Leu Glu Glu Asp Thr Glu Glu Trp Glu Arg Ile
            530                 535                 540

Lys Asn Leu Pro Phe Ala Ile Asp Pro Gln Asn Met Gln Leu Xaa Met
545                 550                 555                 560

Ala Gln Glu Ile Asp Glu Asn Leu Leu Arg Asn Ile Ile Arg Asp Val
            565                 570                 575

Ile Ala Glu Thr Gln Thr Gly Asp Thr Pro Ile Ser Phe Lys Ala Asp
            580                 585                 590

Ala Pro Ala Ala Ser Ser Ala Thr Thr Ala Thr Ala Ala Pro Val Asn
            595                 600                 605

Gly Asp Gly Pro Glu Pro Glu Lys Pro Val Asp Trp Phe Lys His Val
            610                 615                 620

Gly Val Ala Lys Pro Gly Tyr Ser Arg Asp Glu Val Val Ile Ala Val
625                 630                 635                 640

Ala Pro Ala Phe Ala Glu Val Met Asp His Asn Leu Thr Gly Ile Ser
            645                 650                 655

His Lys Glu Ile Leu Arg Gln Met Val Ala Gly Ile Glu Glu Glu Gly
            660                 665                 670

Leu Lys Ala Arg Ile Val Lys Val Tyr Arg Thr Ser Asp Val Ser Phe
            675                 680                 685

Cys Gly Ala Glu Gly Asp His Leu Ser Gly Ser Gly Ile Ala Ile Ala
            690                 695                 700

Ile Gln Ser Lys Gly Thr Thr Ile Ile His Gln Lys Asp Gln Glu Pro
705                 710                 715                 720

Leu Ser Asn Leu Glu Leu Phe Pro Gln Ala Pro Val Leu Asp Gly Asp
            725                 730                 735

Thr Tyr Arg Ala Ile Gly Lys Asn Ala Ala Glu Tyr Ala Lys Gly Met
            740                 745                 750

Ser Pro Ser Pro Val Pro Thr Val Asn Asp Gln Met Ala Arg Val Gln
            755                 760                 765

Tyr Gln Ala Leu Ser Ala Leu Met His Ile Lys Glu Thr Lys Gln Val
            770                 775                 780

Val Met Gly Lys Pro Ala Glu Gln Ile Glu Val Asn Phe Asn Xaa Met
785                 790                 795                 800

Ser Glu Ile Asp Asp Leu Val Ala Lys Ile Val Gln Gln Ile Gly Gly
            805                 810                 815

Thr Glu Ala Ala Asp Gln Thr Thr Ala Thr Pro Thr Ser Thr Ala Thr
            820                 825                 830

Gln Thr Gln His Ala Ala Leu Ser Lys Gln Asp Tyr Pro Leu Tyr Ser
            835                 840                 845

Lys His Pro Glu Leu Val His Ser Pro Ser Gly Lys Ala Leu Asn Asp
            850                 855                 860

Ile Thr Leu Asp Asn Val Leu Asn Asp Asp Ile Lys Ala Asn Asp Leu
865                 870                 875                 880

Arg Ile Thr Pro Asp Thr Leu Arg Met Gln Gly Glu Val Ala Asn Asp
            885                 890                 895
```

```
Ala Gly Arg Asp Ala Val Gln Arg Asn Phe Gln Arg Ala Ser Glu Leu
            900                 905                 910

Thr Ser Ile Pro Asp Asp Arg Leu Leu Glu Met Tyr Asn Ala Leu Arg
            915                 920                 925

Pro Tyr Arg Ser Thr Lys Ala Glu Leu Leu Ala Ile Ser Ala Glu Leu
            930                 935                 940

Lys Asp Lys Tyr His Ala Pro Val Asn Ala Gly Trp Phe Ala Glu Ala
945                 950                 955                 960

Ala Asp Tyr Tyr Glu Ser Arg Lys Lys Leu Lys Gly Asp Asn
            965                 970

<210> SEQ ID NO 20
<211> LENGTH: 974
<212> TYPE: PRT
<213> ORGANISM: Artificial Sequence
<220> FEATURE:
<223> OTHER INFORMATION: AMINO ACID OF DDH:Q337A
<220> FEATURE:
<221> NAME/KEY: MISC_FEATURE
<222> LOCATION: (1)..(974)
<223> OTHER INFORMATION: all Xaa is independently any amino acid

<400> SEQUENCE: 20

Met Lys Arg Gln Lys Arg Phe Glu Glu Leu Glu Lys Arg Pro Ile His
1               5                   10                  15

Leu Asp Gly Phe Val Lys Glu Trp Pro Glu Gly Phe Val Ala Met
            20                  25                  30

Met Gly Pro Asn Asp Pro Lys Pro Ser Ile Lys Ile Glu Asn Gly Lys
            35                  40                  45

Val Thr Glu Met Asp Ser Lys Pro Ala Ala Asp Phe Asp Leu Ile Asp
    50                  55                  60

Leu Tyr Ile Ala Lys Tyr Gly Ile Lys Leu Glu Asn Ala Glu Lys Val
65                  70                  75                  80

Met Ala Met Asp Ser Thr Lys Ile Ala Asn Met Leu Cys Asp Pro Asn
                85                  90                  95

Val Pro Arg Lys Asp Ile Ile Glu Ile Thr Thr Ala Met Thr Pro Ala
            100                 105                 110

Lys Ala Glu Glu Val Ile Ser Lys Leu Asn Phe Ala Glu Met Ile Met
            115                 120                 125

Ala Thr Gln Lys Met Arg Pro Arg Arg Thr Pro Ala Thr Gln Cys His
            130                 135                 140

Val Thr Asn Ile Arg Asp Asn Pro Val Gln Ile Ala Ala Asp Ala Ala
145                 150                 155                 160

Asp Ala Ala Leu Arg Gly Phe Pro Glu Gln Glu Thr Thr Thr Ala Val
                165                 170                 175

Ala Arg Tyr Ala Pro Leu Asn Ala Ile Ser Leu Met Val Gly Ala Gln
            180                 185                 190

Thr Gly Arg Pro Gly Val Ile Thr Gln Cys Ser Val Glu Glu Ala Glu
            195                 200                 205

Glu Leu Ser Leu Gly Met Arg Gly Phe Thr Gly Tyr Ala Glu Thr Ile
            210                 215                 220

Ser Val Tyr Gly Thr Asp Lys Val Phe Thr Asp Gly Asp Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ser Gly Ser Glu Val Met Met Gly Tyr Thr
            260                 265                 270
```

```
Glu Gly Lys Ser Met Leu Tyr Leu Glu Ser Arg Cys Ile Phe Ile Thr
        275                 280                 285
Lys Ala Ser Gly Val Gln Gly Leu Gln Asn Gly Gly Val Ser Cys Ile
    290                 295                 300
Gly Ile Pro Gly Ser Val Pro Ser Gly Ile Arg Ser Val Leu Gly Glu
305                 310                 315                 320
Asn Leu Leu Cys Met Met Leu Asp Leu Glu Cys Ala Ser Ala Asn Asp
                325                 330                 335
Ala Ala Phe Ser His Ser Asp Met Arg Arg Thr Glu Arg Leu Leu Gly
            340                 345                 350
Gln Phe Ile Ala Gly Thr Asp Tyr Ile Ser Ser Gly Tyr Ser Ser Thr
        355                 360                 365
Pro Asn Tyr Asp Asn Thr Phe Ala Gly Ser Asn Thr Asp Gly Leu Asp
370                 375                 380
Tyr Asp Asp Tyr Tyr Val Met Glu Arg Asp Leu Ala Ile Asn Gly Gly
385                 390                 395                 400
Ile His Pro Val Asp Glu Gln Thr Ile Ile Lys Ala Arg Asn Lys Ala
                405                 410                 415
Ala Arg Ala Leu Gln Gly Val Phe Glu Asp Leu Gly Leu Pro Lys Ile
            420                 425                 430
Thr Asp Glu Glu Val Glu Ala Ala Thr Tyr Ala Asn Thr Ser Lys Asp
        435                 440                 445
Met Pro Glu Arg Asn Met Val Glu Asp Met Lys Ala Ala Gln Asp Leu
450                 455                 460
Met Asp Arg Gly Ile Thr Gly Val Asp Ile Val Lys Ala Leu Phe Asn
465                 470                 475                 480
His Gly Phe Lys Asp Val Ala Gln Ala Val Leu Asp Leu Gln Lys Gln
                485                 490                 495
Lys Val Cys Gly Asp Phe Leu Gln Thr Ser Ala Ile Phe Asp Ser Lys
            500                 505                 510
Trp His Val Ile Ser Ala Val Asn Asp Ala Asn Asp Tyr Gln Gly Pro
        515                 520                 525
Gly Thr Gly Tyr Arg Leu Glu Glu Asp Thr Glu Glu Trp Glu Arg Ile
530                 535                 540
Lys Asn Leu Pro Phe Ala Ile Asp Pro Gln Asn Met Gln Leu Xaa Met
545                 550                 555                 560
Ala Gln Glu Ile Asp Glu Asn Leu Leu Arg Asn Ile Ile Arg Asp Val
                565                 570                 575
Ile Ala Glu Thr Gln Thr Gly Asp Thr Pro Ile Ser Phe Lys Ala Asp
            580                 585                 590
Ala Pro Ala Ala Ser Ser Ala Thr Thr Ala Thr Ala Ala Pro Val Asn
        595                 600                 605
Gly Asp Gly Pro Glu Pro Glu Lys Pro Val Asp Trp Phe Lys His Val
610                 615                 620
Gly Val Ala Lys Pro Gly Tyr Ser Arg Asp Glu Val Val Ile Ala Val
625                 630                 635                 640
Ala Pro Ala Phe Ala Glu Val Met Asp His Asn Leu Thr Gly Ile Ser
                645                 650                 655
His Lys Glu Ile Leu Arg Gln Met Val Ala Gly Ile Glu Glu Glu Gly
            660                 665                 670
Leu Lys Ala Arg Ile Val Lys Val Tyr Arg Thr Ser Asp Val Ser Phe
        675                 680                 685
```

```
Cys Gly Ala Glu Gly Asp His Leu Ser Gly Ser Gly Ile Ala Ile Ala
        690                 695                 700
Ile Gln Ser Lys Gly Thr Thr Ile Ile His Gln Lys Asp Gln Glu Pro
705                 710                 715                 720
Leu Ser Asn Leu Glu Leu Phe Pro Gln Ala Pro Val Leu Asp Gly Asp
                725                 730                 735
Thr Tyr Arg Ala Ile Gly Lys Asn Ala Ala Glu Tyr Ala Lys Gly Met
            740                 745                 750
Ser Pro Ser Pro Val Pro Thr Val Asn Asp Gln Met Ala Arg Val Gln
        755                 760                 765
Tyr Gln Ala Leu Ser Ala Leu Met His Ile Lys Glu Thr Lys Gln Val
770                 775                 780
Val Met Gly Lys Pro Ala Glu Gln Ile Glu Val Asn Phe Asn Xaa Met
785                 790                 795                 800
Ser Glu Ile Asp Asp Leu Val Ala Lys Ile Val Gln Ile Gly Gly
                805                 810                 815
Thr Glu Ala Ala Asp Gln Thr Thr Ala Thr Pro Thr Ser Thr Ala Thr
            820                 825                 830
Gln Thr Gln His Ala Ala Leu Ser Lys Gln Asp Tyr Pro Leu Tyr Ser
        835                 840                 845
Lys His Pro Glu Leu Val His Ser Pro Ser Gly Lys Ala Leu Asn Asp
850                 855                 860
Ile Thr Leu Asp Asn Val Leu Asn Asp Asp Ile Lys Ala Asn Asp Leu
865                 870                 875                 880
Arg Ile Thr Pro Asp Thr Leu Arg Met Gln Gly Glu Val Ala Asn Asp
                885                 890                 895
Ala Gly Arg Asp Ala Val Gln Arg Asn Phe Gln Arg Ala Ser Glu Leu
            900                 905                 910
Thr Ser Ile Pro Asp Asp Arg Leu Leu Glu Met Tyr Asn Ala Leu Arg
        915                 920                 925
Pro Tyr Arg Ser Thr Lys Ala Glu Leu Leu Ala Ile Ser Ala Glu Leu
        930                 935                 940
Lys Asp Lys Tyr His Ala Pro Val Asn Ala Gly Trp Phe Ala Glu Ala
945                 950                 955                 960
Ala Asp Tyr Tyr Glu Ser Arg Lys Lys Leu Lys Gly Asp Asn
                965                 970
```

<210> SEQ ID NO 21
<211> LENGTH: 974
<212> TYPE: PRT
<213> ORGANISM: Artificial Sequence
<220> FEATURE:
<223> OTHER INFORMATION: AMINO ACID OF DDH: F375I
<220> FEATURE:
<221> NAME/KEY: MISC_FEATURE
<222> LOCATION: (1)..(974)
<223> OTHER INFORMATION: all Xaa is independently any amino acid

<400> SEQUENCE: 21

```
Met Lys Arg Gln Lys Arg Phe Glu Glu Leu Glu Lys Arg Pro Ile His
1               5                   10                  15
Leu Asp Gly Phe Val Lys Glu Trp Pro Glu Gly Phe Val Ala Met
            20                  25                  30
Met Gly Pro Asn Asp Pro Lys Pro Ser Ile Lys Ile Glu Asn Gly Lys
        35                  40                  45
Val Thr Glu Met Asp Ser Lys Pro Ala Ala Asp Phe Asp Leu Ile Asp
50                  55                  60
```

```
Leu Tyr Ile Ala Lys Tyr Gly Ile Lys Leu Glu Asn Ala Glu Lys Val
 65                  70                  75                  80

Met Ala Met Asp Ser Thr Lys Ile Ala Asn Met Leu Cys Asp Pro Asn
                 85                  90                  95

Val Pro Arg Lys Asp Ile Ile Glu Ile Thr Thr Ala Met Thr Pro Ala
            100                 105                 110

Lys Ala Glu Glu Val Ile Ser Lys Leu Asn Phe Ala Glu Met Ile Met
        115                 120                 125

Ala Thr Gln Lys Met Arg Pro Arg Thr Pro Ala Thr Gln Cys His
130                 135                 140

Val Thr Asn Ile Arg Asp Asn Pro Val Gln Ile Ala Ala Asp Ala Ala
145                 150                 155                 160

Asp Ala Ala Leu Arg Gly Phe Pro Glu Gln Glu Thr Thr Thr Ala Val
                165                 170                 175

Ala Arg Tyr Ala Pro Leu Asn Ala Ile Ser Leu Met Val Gly Ala Gln
            180                 185                 190

Thr Gly Arg Pro Gly Val Ile Thr Gln Cys Ser Val Glu Glu Ala Glu
        195                 200                 205

Glu Leu Ser Leu Gly Met Arg Gly Phe Thr Gly Tyr Ala Glu Thr Ile
210                 215                 220

Ser Val Tyr Gly Thr Asp Lys Val Phe Thr Asp Gly Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ser Ser Glu Val Met Met Gly Tyr Thr
            260                 265                 270

Glu Gly Lys Ser Met Leu Tyr Leu Glu Ser Arg Cys Ile Phe Ile Thr
        275                 280                 285

Lys Ala Ser Gly Val Gln Gly Leu Gln Asn Gly Gly Val Ser Cys Ile
290                 295                 300

Gly Ile Pro Gly Ser Val Pro Ser Gly Ile Arg Ser Val Leu Gly Glu
305                 310                 315                 320

Asn Leu Leu Cys Met Met Leu Asp Leu Glu Cys Ala Ser Ala Asn Asp
                325                 330                 335

Gln Ala Phe Ser His Ser Asp Met Arg Arg Thr Glu Arg Leu Leu Gly
            340                 345                 350

Gln Phe Ile Ala Gly Thr Asp Tyr Ile Ser Ser Gly Tyr Ser Ser Thr
        355                 360                 365

Pro Asn Tyr Asp Asn Thr Ile Ala Gly Ser Asn Thr Asp Gly Leu Asp
370                 375                 380

Tyr Asp Asp Tyr Tyr Val Met Glu Arg Asp Leu Ala Ile Asn Gly Gly
385                 390                 395                 400

Ile His Pro Val Asp Glu Gln Thr Ile Ile Lys Ala Arg Asn Lys Ala
                405                 410                 415

Ala Arg Ala Leu Gln Gly Val Phe Glu Asp Leu Gly Leu Pro Lys Ile
            420                 425                 430

Thr Asp Glu Glu Val Glu Ala Ala Thr Tyr Ala Asn Thr Ser Lys Asp
        435                 440                 445

Met Pro Glu Arg Asn Met Val Glu Asp Met Lys Ala Ala Gln Asp Leu
450                 455                 460

Met Asp Arg Gly Ile Thr Gly Val Asp Ile Val Lys Ala Leu Phe Asn
465                 470                 475                 480
```

```
His Gly Phe Lys Asp Val Ala Gln Ala Val Leu Asp Leu Gln Lys Gln
            485                 490                 495

Lys Val Cys Gly Asp Phe Leu Gln Thr Ser Ala Ile Phe Asp Ser Lys
        500                 505                 510

Trp His Val Ile Ser Ala Val Asn Asp Ala Asn Asp Tyr Gln Gly Pro
            515                 520                 525

Gly Thr Gly Tyr Arg Leu Glu Glu Asp Thr Glu Glu Trp Glu Arg Ile
        530                 535                 540

Lys Asn Leu Pro Phe Ala Ile Asp Pro Gln Asn Met Gln Leu Xaa Met
545                 550                 555                 560

Ala Gln Glu Ile Asp Glu Asn Leu Leu Arg Asn Ile Ile Arg Asp Val
                565                 570                 575

Ile Ala Glu Thr Gln Thr Gly Asp Thr Pro Ile Ser Phe Lys Ala Asp
            580                 585                 590

Ala Pro Ala Ala Ser Ser Ala Thr Thr Ala Thr Ala Ala Pro Val Asn
        595                 600                 605

Gly Asp Gly Pro Glu Pro Glu Lys Pro Val Asp Trp Phe Lys His Val
    610                 615                 620

Gly Val Ala Lys Pro Gly Tyr Ser Arg Asp Glu Val Val Ile Ala Val
625                 630                 635                 640

Ala Pro Ala Phe Ala Glu Val Met Asp His Asn Leu Thr Gly Ile Ser
                645                 650                 655

His Lys Glu Ile Leu Arg Gln Met Val Ala Gly Ile Glu Glu Glu Gly
            660                 665                 670

Leu Lys Ala Arg Ile Val Lys Val Tyr Arg Thr Ser Asp Val Ser Phe
        675                 680                 685

Cys Gly Ala Glu Gly Asp His Leu Ser Gly Ser Gly Ile Ala Ile Ala
    690                 695                 700

Ile Gln Ser Lys Gly Thr Thr Ile Ile His Gln Lys Asp Gln Glu Pro
705                 710                 715                 720

Leu Ser Asn Leu Glu Leu Phe Pro Gln Ala Pro Val Leu Asp Gly Asp
                725                 730                 735

Thr Tyr Arg Ala Ile Gly Lys Asn Ala Ala Glu Tyr Ala Lys Gly Met
            740                 745                 750

Ser Pro Ser Pro Val Pro Thr Val Asn Asp Gln Met Ala Arg Val Gln
        755                 760                 765

Tyr Gln Ala Leu Ser Ala Leu Met His Ile Lys Glu Thr Lys Gln Val
    770                 775                 780

Val Met Gly Lys Pro Ala Glu Gln Ile Glu Val Asn Phe Asn Xaa Met
785                 790                 795                 800

Ser Glu Ile Asp Asp Leu Val Ala Lys Ile Val Gln Gln Ile Gly Gly
                805                 810                 815

Thr Glu Ala Ala Asp Gln Thr Thr Ala Thr Pro Thr Ser Thr Ala Thr
            820                 825                 830

Gln Thr Gln His Ala Ala Leu Ser Lys Gln Asp Tyr Pro Leu Tyr Ser
        835                 840                 845

Lys His Pro Glu Leu Val His Ser Pro Ser Gly Lys Ala Leu Asn Asp
    850                 855                 860

Ile Thr Leu Asp Asn Val Leu Asn Asp Ile Lys Ala Asn Asp Leu
865                 870                 875                 880

Arg Ile Thr Pro Asp Thr Leu Arg Met Gln Gly Glu Val Ala Asn Asp
                885                 890                 895

Ala Gly Arg Asp Ala Val Gln Arg Asn Phe Gln Arg Ala Ser Glu Leu
```

```
                900              905             910
Thr Ser Ile Pro Asp Asp Arg Leu Leu Glu Met Tyr Asn Ala Leu Arg
            915                 920                 925

Pro Tyr Arg Ser Thr Lys Ala Glu Leu Leu Ala Ile Ser Ala Glu Leu
            930                 935                 940

Lys Asp Lys Tyr His Ala Pro Val Asn Ala Gly Trp Phe Ala Glu Ala
945                 950                 955                 960

Ala Asp Tyr Tyr Glu Ser Arg Lys Lys Leu Lys Gly Asp Asn
                965                 970
```

<210> SEQ ID NO 22
<211> LENGTH: 2957
<212> TYPE: DNA
<213> ORGANISM: Artificial Sequence
<220> FEATURE:
<223> OTHER INFORMATION: DDH:Q337A/F375I

<400> SEQUENCE: 22

| | |
|---|---|
| atgaaacgtc aaaaacgatt tgaagaatta gagaaacgcc cgatccattt agacggtttc | 60 |
| gttaaggaat ggcctgaaga aggcttcgtt gccatgatgg ggcctaatga cccaaagcca | 120 |
| agcatcaaga ttgaaaacgg caaggttact gaaatggata gtaaaccagc tgctgacttc | 180 |
| gatctgattg atctctacat cgcaaaatat ggcattaagc ttgaaaatgc tgagaaagta | 240 |
| atggcgatgg attccactaa gatcgccaat atgctctgtg accccaatgt gccacgtaaa | 300 |
| gacatcattg agattacaac ggcgatgacg ccggccaaag ctgaagaagt tatcagcaaa | 360 |
| ttgaactttg ccgaaatgat tatggcaacg caaaaaatgc ggccacggcg gacaccagca | 420 |
| acgcaatgtc acgttaccaa tattcgggat aatcccgttc aaattgctgc tgacgctgcc | 480 |
| gatgctgcct acggggtttt cccggaacaa gaaaccacga cggccgttgc ccggtatgcc | 540 |
| ccattgaatg ccatctcgtt gatggtgggg cgcaaaccg tcgtcctgg tgttatcacc | 600 |
| caatgctcgg ttgaagaagc agaagaattg agtttaggga tgcggggctt cactggctac | 660 |
| gccgaaacca tttctgttta cggtaccgat aaggtcttca ctgatggtga tgatacacca | 720 |
| tggtccaaag gcttcttagc ttcctgctat gcttcgcggg ggttgaagat gcggtttacg | 780 |
| tctggttctg gttccgaagt tatgatgggt tataccgaag gtaagtccat gttataccct | 840 |
| gaatcacgtt gtatcttcat taccaaagcg tccggtgttc aaggcctcca aaacggtggg | 900 |
| gttagttgta ttgggattcc agggtctgtt ccttctggga ttcgctccgt cttgggtgaa | 960 |
| aacctattgt gcatgatgct tgaccttgaa tgtgcgtctg ctaatgacgc agcgttctcc | 1020 |
| cattctgata tgcggcggac agaacggtta ttaggccaat tcattgccgg aaccgattac | 1080 |
| atttcttctg ttactcctc aacacctaac tatgacaaca cgattgcggg gtcaaacacc | 1140 |
| gatggcttgg actacgatga ttactacgtt atggaacgcg acttggccat caacggtggg | 1200 |
| attcacccag ttgatgaaca aacaatcatc aaagcccgca acaaggctgc acgggccctt | 1260 |
| caaggtgtct ttgaagatct aggtttgcct aagattaccg atgaagaagt ggaagcggca | 1320 |
| acttacgcca acacctctaa ggatatgcca gaacggaaca tggttgaaga tatgaaggcc | 1380 |
| gcccaagatc tgatggatcg cggcattacc ggggtcgata ttgttaaagc cttgttcaac | 1440 |
| cacggatttta aggatgttgc ccaagccgtt ttagatttgc aaaagcaaaa ggtttgtggg | 1500 |
| gacttcttac agacatccgc tattttcgac agcaagtggc atgtcatttc gccgtcaac | 1560 |
| gatgccaatg actatcaagg tcctggtacg ggttaccggt tggaagaaga tacggaagaa | 1620 |
| tgggaacgca tcaagaactt accgtttgcc attgatccac aaaacatgca gctttagtcg | 1680 |

-continued

```
aaaaggggt taacactatg gctcaagaaa ttgatgaaaa cttattgcgg aatattatcc    1740
gtgatgtgat tgcggaaacc caaacggggg acacgccaat ctcatttaaa gctgatgcac    1800
cagcagcgtc atcagctacg acggcaacgg ctgcaccagt taatggtgac ggcccagaac    1860
cggaaaaacc agttgactgg ttcaaacacg ttggggttgc caagcccggc tattcacgtg    1920
atgaagtcgt gattgctgtg caccagcct ttgcagaagt gatggaccat aacttgaccg    1980
gaatcagtca taaagaaatt ttacgacaga tggttgctgg tattgaagaa gaaggactga    2040
aggcccgaat tgtgaaagtc taccggactt ctgacgtttc cttctgtggt gccgaagggg    2100
atcatttatc aggttctggc atcgccattg ccattcaatc aaggggacg acgatcattc    2160 accaaaagga ccaagaacca ttgtccaact tggaattatt cccacaagca cctgtcttgg    2220
atggtgatac ctaccgggct atcggcaaga atgcagccga atacgctaaa ggaatgtcac    2280
caagccccgt tccaacggtt aatgaccaaa tggctcgggt tcaataccag gccttgtctg    2340
ccttgatgca tatcaaggaa acgaagcagg tcgttatggg gaaacccgct gaacaaatcg    2400
aagtcaactt taactaggag gaatgggtca tgagtgaaat tgatgactta gtagcaaaaa    2460
tcgtccaaca aattggtggc actgaggccg ctgatcagac gactgccacg cctacgtcaa    2520
cggcgacgca gacgcagcat gcagcattat cgaaacaaga ttatccactg tactctaagc    2580
acccagagct cgtacattca ccgtctggga aagctttgaa cgatatcact ttggataatg    2640
ttctcaacga tgatattaag gccaatgatt tacgaattac gccggatacc ttacggatgc    2700
aaggtgaagt ggccaacgat gctggtcggg atgcggttca acgtaacttc cagcgggcgt    2760
cagaattgac ctctattccg gatgatcggt tactggaaat gtacaacgcc ttacgaccat    2820
accggtctac taaagcggaa ttattagcga tttcagccga gttaaaggat aaatatcatg    2880
ccccagtgaa cgccggatgg tttgcggaag cggccgacta ctacgaatcc cgtaagaagc    2940
tgaagggtga taactag                                                  2957
```

<210> SEQ ID NO 23
<211> LENGTH: 974
<212> TYPE: PRT
<213> ORGANISM: Artificial Sequence
<220> FEATURE:
<223> OTHER INFORMATION: AMINO ACID OF DDH:Q337A/F375I
<220> FEATURE:
<221> NAME/KEY: MISC_FEATURE
<222> LOCATION: (1)..(974)
<223> OTHER INFORMATION: all Xaa is independently any amino acid

<400> SEQUENCE: 23

```
Met Lys Arg Gln Lys Arg Phe Glu Glu Leu Glu Lys Arg Pro Ile His
1               5                   10                  15

Leu Asp Gly Phe Val Lys Glu Trp Pro Glu Gly Phe Val Ala Met
            20                  25                  30

Met Gly Pro Asn Asp Pro Lys Pro Ser Ile Lys Ile Glu Asn Gly Lys
        35                  40                  45

Val Thr Glu Met Asp Ser Lys Pro Ala Ala Asp Phe Asp Leu Ile Asp
    50                  55                  60

Leu Tyr Ile Ala Lys Tyr Gly Ile Lys Leu Glu Asn Ala Glu Lys Val
65                  70                  75                  80

Met Ala Met Asp Ser Thr Lys Ile Ala Asn Met Leu Cys Asp Pro Asn
                85                  90                  95

Val Pro Arg Lys Asp Ile Ile Glu Ile Thr Thr Ala Met Thr Pro Ala
            100                 105                 110
```

```
Lys Ala Glu Glu Val Ile Ser Lys Leu Asn Phe Ala Glu Met Ile Met
            115                 120                 125
Ala Thr Gln Lys Met Arg Pro Arg Thr Pro Ala Thr Gln Cys His
130                 135                 140
Val Thr Asn Ile Arg Asp Asn Pro Val Gln Ile Ala Ala Asp Ala Ala
145                 150                 155                 160
Asp Ala Ala Leu Arg Gly Phe Pro Gln Glu Thr Thr Thr Ala Val
                165                 170                 175
Ala Arg Tyr Ala Pro Leu Asn Ala Ile Ser Leu Met Val Gly Ala Gln
                180                 185                 190
Thr Gly Arg Pro Gly Val Ile Thr Gln Cys Ser Val Glu Glu Ala Glu
            195                 200                 205
Glu Leu Ser Leu Gly Met Arg Gly Phe Thr Gly Tyr Ala Glu Thr Ile
            210                 215                 220
Ser Val Tyr Gly Thr Asp Lys Val Phe Thr Asp Gly Asp Thr Pro
225                 230                 235                 240
Trp Ser Lys Gly Phe Leu Ala Ser Cys Tyr Ala Ser Arg Gly Leu Lys
                245                 250                 255
Met Arg Phe Thr Ser Gly Ser Gly Ser Glu Val Met Met Gly Tyr Thr
            260                 265                 270
Glu Gly Lys Ser Met Leu Tyr Leu Glu Ser Arg Cys Ile Phe Ile Thr
            275                 280                 285
Lys Ala Ser Gly Val Gln Gly Leu Gln Asn Gly Gly Val Ser Cys Ile
            290                 295                 300
Gly Ile Pro Gly Ser Val Pro Ser Gly Ile Arg Ser Val Leu Gly Glu
305                 310                 315                 320
Asn Leu Leu Cys Met Met Leu Asp Leu Glu Cys Ala Ser Ala Asn Asp
                325                 330                 335
Ala Ala Phe Ser His Ser Asp Met Arg Arg Thr Glu Arg Leu Leu Gly
                340                 345                 350
Gln Phe Ile Ala Gly Thr Asp Tyr Ile Ser Ser Gly Tyr Ser Ser Thr
            355                 360                 365
Pro Asn Tyr Asp Asn Thr Ile Ala Gly Ser Asn Thr Asp Gly Leu Asp
            370                 375                 380
Tyr Asp Asp Tyr Tyr Val Met Glu Arg Asp Leu Ala Ile Asn Gly Gly
385                 390                 395                 400
Ile His Pro Val Asp Glu Gln Thr Ile Ile Lys Ala Arg Asn Lys Ala
                405                 410                 415
Ala Arg Ala Leu Gln Gly Val Phe Glu Asp Leu Gly Leu Pro Lys Ile
                420                 425                 430
Thr Asp Glu Glu Val Glu Ala Ala Thr Tyr Ala Asn Thr Ser Lys Asp
            435                 440                 445
Met Pro Glu Arg Asn Met Val Glu Asp Met Lys Ala Ala Gln Asp Leu
            450                 455                 460
Met Asp Arg Gly Ile Thr Gly Val Asp Ile Val Lys Ala Leu Phe Asn
465                 470                 475                 480
His Gly Phe Lys Asp Val Ala Gln Ala Val Leu Asp Leu Gln Lys Gln
                485                 490                 495
Lys Val Cys Gly Asp Phe Leu Gln Thr Ser Ala Ile Phe Asp Ser Lys
            500                 505                 510
Trp His Val Ile Ser Ala Val Asn Asp Ala Asn Asp Tyr Gln Gly Pro
            515                 520                 525
```

```
Gly Thr Gly Tyr Arg Leu Glu Glu Asp Thr Glu Glu Trp Glu Arg Ile
            530                 535                 540

Lys Asn Leu Pro Phe Ala Ile Asp Pro Gln Asn Met Gln Leu Xaa Met
545                 550                 555                 560

Ala Gln Glu Ile Asp Glu Asn Leu Leu Arg Asn Ile Ile Arg Asp Val
                565                 570                 575

Ile Ala Glu Thr Gln Thr Gly Asp Thr Pro Ile Ser Phe Lys Ala Asp
            580                 585                 590

Ala Pro Ala Ala Ser Ser Ala Thr Thr Ala Thr Ala Ala Pro Val Asn
            595                 600                 605

Gly Asp Gly Pro Glu Pro Glu Lys Pro Val Asp Trp Phe Lys His Val
610                 615                 620

Gly Val Ala Lys Pro Gly Tyr Ser Arg Asp Glu Val Val Ile Ala Val
625                 630                 635                 640

Ala Pro Ala Phe Ala Glu Val Met Asp His Asn Leu Thr Gly Ile Ser
                645                 650                 655

His Lys Glu Ile Leu Arg Gln Met Val Ala Gly Ile Glu Glu Glu Gly
                660                 665                 670

Leu Lys Ala Arg Ile Val Lys Val Tyr Arg Thr Ser Asp Val Ser Phe
            675                 680                 685

Cys Gly Ala Glu Gly Asp His Leu Ser Gly Ser Gly Ile Ala Ile Ala
690                 695                 700

Ile Gln Ser Lys Gly Thr Thr Ile Ile His Gln Lys Asp Gln Glu Pro
705                 710                 715                 720

Leu Ser Asn Leu Glu Leu Phe Pro Gln Ala Pro Val Leu Asp Gly Asp
                725                 730                 735

Thr Tyr Arg Ala Ile Gly Lys Asn Ala Ala Glu Tyr Ala Lys Gly Met
            740                 745                 750

Ser Pro Ser Pro Val Pro Thr Val Asn Asp Gln Met Ala Arg Val Gln
            755                 760                 765

Tyr Gln Ala Leu Ser Ala Leu Met His Ile Lys Glu Thr Lys Gln Val
            770                 775                 780

Val Met Gly Lys Pro Ala Glu Gln Ile Glu Val Asn Phe Asn Xaa Met
785                 790                 795                 800

Ser Glu Ile Asp Asp Leu Val Ala Lys Ile Val Gln Ile Gly Gly
                805                 810                 815

Thr Glu Ala Ala Asp Gln Thr Thr Ala Thr Pro Thr Ser Thr Ala Thr
                820                 825                 830

Gln Thr Gln His Ala Ala Leu Ser Lys Gln Asp Tyr Pro Leu Tyr Ser
            835                 840                 845

Lys His Pro Glu Leu Val His Ser Pro Ser Gly Lys Ala Leu Asn Asp
850                 855                 860

Ile Thr Leu Asp Asn Val Leu Asn Asp Ile Lys Ala Asn Asp Leu
865                 870                 875                 880

Arg Ile Thr Pro Asp Thr Leu Arg Met Gln Gly Glu Val Ala Asn Asp
                885                 890                 895

Ala Gly Arg Asp Ala Val Gln Arg Asn Phe Gln Arg Ala Ser Glu Leu
            900                 905                 910

Thr Ser Ile Pro Asp Asp Arg Leu Leu Glu Met Tyr Asn Ala Leu Arg
            915                 920                 925

Pro Tyr Arg Ser Thr Lys Ala Glu Leu Leu Ala Ile Ser Ala Glu Leu
930                 935                 940

Lys Asp Lys Tyr His Ala Pro Val Asn Ala Gly Trp Phe Ala Glu Ala
```

|  |  |  | 945 |  |  | 950 |  |  | 955 |  |  | 960 |
| --- | --- | --- | --- | --- | --- | --- | --- | --- | --- | --- | --- | --- |
| Ala | Asp | Tyr | Tyr | Glu | Ser | Arg | Lys | Lys | Leu | Lys | Gly | Asp | Asn |
|  |  |  |  |  | 965 |  |  |  | 970 |  |  |  |  |

<210> SEQ ID NO 24
<211> LENGTH: 2185
<212> TYPE: DNA
<213> ORGANISM: Artificial Sequence
<220> FEATURE:
<223> OTHER INFORMATION: Full-length dhaR

<400> SEQUENCE: 24

```
atgcaaaagg tgataggtgt agatattggt aattcctcaa cggaagttgc tttggctgat    60
atttcagatc aaggtgcggt tgattttatc aattctgaca ttgcagagac cacggggatc   120
aaaggaacta agcaaaacct cattgggatc aaaaaagcca ttacgcaggt gttaaataaa   180
agtcatttag ccttgagtga tattgacctg attcggatta cgaagcaac accggttatt   240
ggggatgtag cgatggaaac catcacggaa acagtgatta ctgaatccac gatgattggg   300
cataacccga cacaccagg tggcgtcggc attggttctg ctatacggt gaatttgcta   360
caactgcttc aagaaaccga taagactcgt ccgtacattg ttctggtacc ggctgaagtt   420
gatttcgaag atgcggctaa gctgatcaat ctataccagc aaagtggtta tcaaataact   480
gcggccatcc tgcaaaatga cgatggggtg ttaattgata ccgattgga cataagata   540
ccaattgtag atgaagtggc gcggattgat aaggttccca tggggatgat ggctggcgtt   600
gaggttgctg gtaaagggca agttatttcg cagttatcta atccgtatgg gatcgccacg   660
ctctttgatt tgacggccga tgaaaccaaa aacatcgtgc cggtttctcg ggcgttaatt   720
ggcaaccggt ctgcggtggt catcaagacg cctaagggg atgtgaaggc ccgggttatt   780
ccggccggga gcatccaaat cgaaggtgat cgagattctg acaaggttaa cgtggccgct   840
ggtgctgaag caattatgaa gaaggtcaat cagtttgacc ggattcaaga tattacaggt   900
gaagcgggaa ccaatgttgg tgggatgttg aaaaggttc ggcagacgat ggcggacctc   960
accaacaaac agaacagaga tatcgctatt caagatctgt tagccgtcaa cacggcggtt  1020
ccagtcaagg tacaaggtgg actggctggc gagttctcaa ccgaacaagc cgttgggatt  1080
gccgcaatgg taaaatctga ccacctccag atgcaacaga ttgctgattt gattcaagac  1140
gagcttcaca tttccgttga gattggcgga gctgaagctg aggccgcaat cttgggagct  1200
ttgacgacac aggaacaac caagcccatt gcgattcttg acttgggtgc cggttcaaca  1260
gatgcctcga ttatcaatca gcaagatgat attgtggcga ttcacttggc tggtgccggg  1320
gacatggtca ccatgattat caattctgag ttaggcctag acgatgtgta cttggccgag  1380
gatattaaga aatatccgct ggcccgagtt gaaaatctat tccaaattcg gcatgaagat  1440
ggcacggttc agtttttga agacccactg ccagcagaca ttttgcccg cacagtggtc  1500
attaagccgg acggttacgt cccattacca gggaatatga acattgaaaa ggttaagcag  1560
attcgccaga ccgctaagaa gcgggtgttt gtggaaaatg cacggcgggc cttacaacac  1620
gtgagtccca ctggtaatat ccgtgacatc ccgtttgtcg tgatcgttgg gggatcggcg  1680
ctggactttg aaatcccaca attggtcacg gatgagttgt ctcactataa ccttgttgcc  1740
ggacggggaa atattcgggc cgtggaagga ccgcgaaatg cggttgctac gggattgatc  1800
ctgtcttatg cccgggagag aagggacgcc tatgaccaac acaatggata aaccggcaat  1860
ttttattgcc gtgccgacag cggcgtccga tttaccggtg actttgaaac cgttacttaa  1920
```

```
cgggattgaa gaagaagcca ttccggtaca gaccaaggtg attgcagaag acgatgtcac    1980
catgcgcact tatcaggcgg ctttggcttc acggttgtcc gtgggcattg gttttgacga    2040
tcagcatgtg gttgttcact acaagaacct gcatgccgag cagccgttat tcacggtgac    2100
ccgtgattcg gcggaccgcc tgcgccggtt aggtgctaat gcagctcgct tggtgaaggg    2160
cgtgcccttt aagacattag attag                                          2185
```

<210> SEQ ID NO 25
<211> LENGTH: 31
<212> TYPE: DNA
<213> ORGANISM: Artificial Sequence
<220> FEATURE:
<223> OTHER INFORMATION: EtDH1 Primer

<400> SEQUENCE: 25

```
gattgttacc ggtgctggcc tgcataaaat g                                     31
```

<210> SEQ ID NO 26
<211> LENGTH: 31
<212> TYPE: DNA
<213> ORGANISM: Artificial Sequence
<220> FEATURE:
<223> OTHER INFORMATION: EtDH2 Primer

<400> SEQUENCE: 26

```
cattttatgc aggccagcac cggtaacaat c                                     31
```

<210> SEQ ID NO 27
<211> LENGTH: 37
<212> TYPE: DNA
<213> ORGANISM: Artificial Sequence
<220> FEATURE:
<223> OTHER INFORMATION: FLS1 Primer
<220> FEATURE:
<221> NAME/KEY: misc_feature
<222> LOCATION: (20)..(22)
<223> OTHER INFORMATION: n is a, c, g, or t

<400> SEQUENCE: 27

```
ggtagcggat ggtggcctgn nntatctctg gctgtcc                               37
```

<210> SEQ ID NO 28
<211> LENGTH: 37
<212> TYPE: DNA
<213> ORGANISM: Artificial Sequence
<220> FEATURE:
<223> OTHER INFORMATION: FLS2 Primer
<220> FEATURE:
<221> NAME/KEY: misc_feature
<222> LOCATION: (16)..(18)
<223> OTHER INFORMATION: n is a, c, g, or t

<400> SEQUENCE: 28

```
ggacagccag agatannnca ggccaccatc cgctacc                               37
```

<210> SEQ ID NO 29
<211> LENGTH: 37
<212> TYPE: DNA
<213> ORGANISM: Artificial Sequence
<220> FEATURE:
<223> OTHER INFORMATION: FLS3 Primer
<220> FEATURE:
<221> NAME/KEY: misc_feature
<222> LOCATION: (20)..(22)
<223> OTHER INFORMATION: n is a, c, g, or t

<400> SEQUENCE: 29

```
ccgccgcacg atccttgtgn nnggcgatgg ctcggtg                              37
```

<210> SEQ ID NO 30
<211> LENGTH: 37
<212> TYPE: DNA
<213> ORGANISM: Artificial Sequence
<220> FEATURE:
<223> OTHER INFORMATION: FLS4 Primer
<220> FEATURE:
<221> NAME/KEY: misc_feature
<222> LOCATION: (16)..(18)
<223> OTHER INFORMATION: n is a, c, g, or t

<400> SEQUENCE: 30

```
caccgagcca tcgccnnnca caaggatcgt gcggcgg                              37
```

<210> SEQ ID NO 31
<211> LENGTH: 37
<212> TYPE: DNA
<213> ORGANISM: Artificial Sequence
<220> FEATURE:
<223> OTHER INFORMATION: FLS5 Primer
<220> FEATURE:
<221> NAME/KEY: misc_feature
<222> LOCATION: (20)..(22)
<223> OTHER INFORMATION: n is a, c, g, or t

<400> SEQUENCE: 31

```
gccgctgatc gtcatcatcn nnaacaacca aagctgg                              37
```

<210> SEQ ID NO 32
<211> LENGTH: 37
<212> TYPE: DNA
<213> ORGANISM: Artificial Sequence
<220> FEATURE:
<223> OTHER INFORMATION: FLS6 Primer
<220> FEATURE:
<221> NAME/KEY: misc_feature
<222> LOCATION: (16)..(18)
<223> OTHER INFORMATION: n is a, c, g, or t

<400> SEQUENCE: 32

```
ccagctttgg ttgttnnnga tgatgacgat cagcggc                              37
```

<210> SEQ ID NO 33
<211> LENGTH: 37
<212> TYPE: DNA
<213> ORGANISM: Artificial Sequence
<220> FEATURE:
<223> OTHER INFORMATION: FLS7 Primer
<220> FEATURE:
<221> NAME/KEY: misc_feature
<222> LOCATION: (20)..(22)
<223> OTHER INFORMATION: n is a, c, g, or t

<400> SEQUENCE: 33

```
catcatcatg aacaaccaan nntgggggtg gacattg                              37
```

<210> SEQ ID NO 34
<211> LENGTH: 37
<212> TYPE: DNA
<213> ORGANISM: Artificial Sequence
<220> FEATURE:
<223> OTHER INFORMATION: FLS8 Primer
<220> FEATURE:
<221> NAME/KEY: misc_feature
<222> LOCATION: (16)..(18)
<223> OTHER INFORMATION: n is a, c, g, or t

```
<400> SEQUENCE: 34
caatgtccac ccccannntt ggttgttcat gatgatg                               37

<210> SEQ ID NO 35
<211> LENGTH: 37
<212> TYPE: DNA
<213> ORGANISM: Artificial Sequence
<220> FEATURE:
<223> OTHER INFORMATION: FLS9 Primer
<220> FEATURE:
<221> NAME/KEY: misc_feature
<222> LOCATION: (20)..(22)
<223> OTHER INFORMATION: n is a, c, g, or t

<400> SEQUENCE: 35
ccaaagctgg gggtggacan nncatttcca gcaattg                               37

<210> SEQ ID NO 36
<211> LENGTH: 37
<212> TYPE: DNA
<213> ORGANISM: Artificial Sequence
<220> FEATURE:
<223> OTHER INFORMATION: FLS10 Primer
<220> FEATURE:
<221> NAME/KEY: misc_feature
<222> LOCATION: (16)..(18)
<223> OTHER INFORMATION: n is a, c, g, or t

<400> SEQUENCE: 36
caattgctgg aaatgnnntg tccacccccca gctttgg                              37

<210> SEQ ID NO 37
<211> LENGTH: 37
<212> TYPE: DNA
<213> ORGANISM: Artificial Sequence
<220> FEATURE:
<223> OTHER INFORMATION: FLS11 Primer
<220> FEATURE:
<221> NAME/KEY: misc_feature
<222> LOCATION: (20)..(22)
<223> OTHER INFORMATION: n is a, c, g, or t

<400> SEQUENCE: 37
tcgcgtgacg ggcacccgtn nngaaaatgg ctcctat                               37

<210> SEQ ID NO 38
<211> LENGTH: 37
<212> TYPE: DNA
<213> ORGANISM: Artificial Sequence
<220> FEATURE:
<223> OTHER INFORMATION: FLS12 Primer
<220> FEATURE:
<221> NAME/KEY: misc_feature
<222> LOCATION: (16)..(18)
<223> OTHER INFORMATION: n is a, c, g, or t

<400> SEQUENCE: 38
ataggagcca ttttcnnnac gggtgcccgt cacgcga                               37

<210> SEQ ID NO 39
<211> LENGTH: 36
<212> TYPE: DNA
<213> ORGANISM: Artificial Sequence
<220> FEATURE:
<223> OTHER INFORMATION: BDH1 primer

<400> SEQUENCE: 39
gaattatcgg tgttggagcc agacctgttt gtgttg                                36
```

<210> SEQ ID NO 40
<211> LENGTH: 36
<212> TYPE: DNA
<213> ORGANISM: Artificial Sequence
<220> FEATURE:
<223> OTHER INFORMATION: BDH2 primer

<400> SEQUENCE: 40
caacacaaac aggtctggct ccaacaccga taattc                    36

<210> SEQ ID NO 41
<211> LENGTH: 37
<212> TYPE: DNA
<213> ORGANISM: Artificial Sequence
<220> FEATURE:
<223> OTHER INFORMATION: DDH1 primer

<400> SEQUENCE: 41
ctccaaaacg gtggggttgc ttgtattggg attccag                   37

<210> SEQ ID NO 42
<211> LENGTH: 37
<212> TYPE: DNA
<213> ORGANISM: Artificial Sequence
<220> FEATURE:
<223> OTHER INFORMATION: DDH2 primer

<400> SEQUENCE: 42
ctggaatccc aatacaagca accccaccgt tttggag                   37

<210> SEQ ID NO 43
<211> LENGTH: 38
<212> TYPE: DNA
<213> ORGANISM: Artificial Sequence
<220> FEATURE:
<223> OTHER INFORMATION: DDH3 primer

<400> SEQUENCE: 43
atgtgcgtct gctaatgacg cagcgttctc ccattctg                  38

<210> SEQ ID NO 44
<211> LENGTH: 38
<212> TYPE: DNA
<213> ORGANISM: Artificial Sequence
<220> FEATURE:
<223> OTHER INFORMATION: DDH4 primer

<400> SEQUENCE: 44
cagaatggga gaacgctgcg tcattagcag acgcacat                  38

<210> SEQ ID NO 45
<211> LENGTH: 39
<212> TYPE: DNA
<213> ORGANISM: Artificial Sequence
<220> FEATURE:
<223> OTHER INFORMATION: DDH5 primer

<400> SEQUENCE: 45
cacctaacta tgacaacacg attgcggggt caaacaccg                 39

<210> SEQ ID NO 46
<211> LENGTH: 39
<212> TYPE: DNA
<213> ORGANISM: Artificial Sequence
<220> FEATURE:

```
<223> OTHER INFORMATION: DDH6 primer

<400> SEQUENCE: 46
cggtgtttga ccccgcaatc gtgttgtcat agttaggtg                                    39
```